US012247979B2

(12) United States Patent
Newman et al.

(10) Patent No.: US 12,247,979 B2
(45) Date of Patent: *Mar. 11, 2025

(54) COMPOSITIONS AND METHODS FOR CAPTURING EXOSOMES

(71) Applicant: Morehouse School of Medicine, Atlanta, GA (US)

(72) Inventors: Gale W. Newman, Duluth, GA (US); Samuel Anyanwu, Atlanta, GA (US); James W. Lillard, Jr., Smyrna, GA (US)

(*) Notice: Subject to any disclaimer, the term of this patent is extended or adjusted under 35 U.S.C. 154(b) by 186 days.

This patent is subject to a terminal disclaimer.

(21) Appl. No.: 18/172,059

(22) Filed: Feb. 21, 2023

(65) Prior Publication Data

US 2023/0341401 A1 Oct. 26, 2023

Related U.S. Application Data

(63) Continuation of application No. 16/566,273, filed on Sep. 10, 2019, now abandoned, which is a continuation of application No. 14/702,372, filed on May 1, 2015, now abandoned.

(51) Int. Cl.
  *G01N 33/573* (2006.01)
  *C07K 16/40* (2006.01)
  *G01N 33/68* (2006.01)

(52) U.S. Cl.
  CPC .......... *G01N 33/573* (2013.01); *C07K 16/40* (2013.01); *G01N 33/6893* (2013.01); *C07K 2317/34* (2013.01); *G01N 2333/91102* (2013.01)

(58) Field of Classification Search
  None
  See application file for complete search history.

(56) References Cited

U.S. PATENT DOCUMENTS

| 10,416,161 | B2 * | 9/2019 | Newman | G01N 33/6893 |
| 11,300,565 | B2 * | 4/2022 | Newman | C12Q 1/70 |
| 2007/0065886 | A1 | 3/2007 | Bowen | |
| 2014/0134606 | A1 | 5/2014 | Newman et al. | |

OTHER PUBLICATIONS

Cheruvanky et al. (Am J Physiol Renal Physiol 292: F1657-F1661, 2007) (Year: 2007).*
Vlassov et al. (Biochimica et Biophysica Acta 1820:940-948, 2012) (Year: 2012).*
International Search Report of Application No. PCT/US2016/030413, mailed Sep. 15, 2016.
Abcam, Product datasheet for Anti-ALG6 antibody ab80873, retrieved from http://abcam.com/alg6-antibody-ab80873.html on Jul. 21, 2017, 2 pages.
Academic Press Dictionary of Science and Technology, definition for the term "polyclonal"; Oxford: Elsevier Science and Technology (1998); retrieved Oct. 22, 2008, from http://www.credoreference.com entry/3144515.
Janeway et al. Immunobiology: the Immune System in Health and Disease (1999), Elsevier Science Ltd/Garland Publishing, New York, NY, Fourth Edition, pp. 34-35.
Harlow, E and Lane, D. Antib A Laboratory Manual (1968) Cold Spring Harbor Laboratory Press, Cold Spring Harbor, NY, pp. 23-24, 72-76, 553, 555-582, and 584-592.
Abcam, Product datasheet for Anti-ALG6 antibody ab57112, retrieved from http://www.abcam.com/alg6-antibody-ab57112.html on Jul. 21, 2017, 2 pages.
File History of U.S. Appl. No. 14/702,372, filed May 1, 2015.

* cited by examiner

*Primary Examiner* — Sharon X Wen
(74) *Attorney, Agent, or Firm* — Ping Wang; Kalos Athena Wang PLLC

(57) ABSTRACT

Compositions and kits for exosome capture include an antibody specifically binding the human asparagine-linked glycosylation 6 homolog (ALG6). The compositions and kits may be employed in a method for diagnosing a disease or condition in a subject.

12 Claims, 11 Drawing Sheets

Specification includes a Sequence Listing.

HIVAN (1:10 dilution)
X 60,000

FSGS
X 60,000

AA HIV+
X 60,000

White HIV+
X 60,000

AA HIV negative
X 60,000

SEQUENCE LISTING

Sequence total quantity: 2
SEQ ID NO: 1          moltype = AA  length = 11
FEATURE               Location/Qualifiers

```
                        -continued source              1..11
                    mol_type = protein
                    organism = Homo sapiens
SEQUENCE: 1
YEAQRHWQEI T                                                          11

SEQ ID NO: 2        moltype = AA  length = 13
FEATURE             Location/Qualifiers
source              1..13
                    mol_type = protein
                    organism = Homo sapiens
SEQUENCE: 2
GDYEAQRHWQ EIT                                                        13
```

COMPOSITIONS AND METHODS FOR CAPTURING EXOSOMES

This application is a Continuation of U.S. application Ser. No. 16/566,273, filed Sep. 10, 2019, which is a Continuation of U.S. application Ser. No. 14/702,372, filed May 1, 2015, now abandoned. The entirety of the aforementioned applications is incorporated herein by reference.

This application was made with government support under certain grants awarded by government agencies. The government has certain rights in the invention.

FIELD

The present invention generally relates to composition for capturing exosomes, in particular, an antibody, for capturing exosomes from bodily fluids and detecting exosome biomarkers for determining conditions or diagnosing diseases, such as, infectious and/or non-infectious diseases.

BACKGROUND

Exosomes are small vesicles 40-100 nm in diameter, that are secreted by a number of different cell types for communicating with other cells via the proteins and ribonucleic acids they carry. An exosome is created intracellularly when a segment of the cell membrane spontaneously invaginates and is endocytosed. The internalized segment is broken into smaller vesicles that are subsequently expelled from the cell. The latter stage occurs when the late endosome, containing many small vesicles, fuses with the cell membrane, triggering the release of the vesicles from the cell. The vesicles (once released are called exosomes) consist of a lipid raft embedded with ligands common to the original cell membrane.

Depending on their cellular origin, exosomes carry uniquely distinct profiles of proteins and/or nucleic acids (such as microRNAs (miRNAs)), which can trigger signaling pathways in other cells and/or transfer exosome products into other cells by exosome fusion with cellular plasma membranes. The protein composition of exosomes is distinct from that of other organelles, including early endosomes and plasma membranes, more closely resembling that of late endosomes or multivesicular bodies (MVBs).

Exosomes are released from different cell types in varied physiological contexts. For example, B lymphocytes release exosomes carrying class II major histocompatibility complex molecules, which play a role in antigenic presentation. Similarly, dendritic cells produce exosomes (i.e., dexosomes, Dex), which play a role in immune response mediation, particularly in cytotoxic T lymphocyte stimulation. Some tumor cells secrete specific exosomes (i.e., texosomes, Tex) carrying tumor antigens in a regulated manner, which can present these antigens to antigen presenting cells. Exosomes may also carry pathogen-associated products. For example, exosomes have been known to carry products derived from *Mycobacterium tuberculosis* and *Toxoplasma gondii*-infected cells.

Disease conditions are often assayed using serum or plasma. For example, the detection of a specific viral antibody is presumptive evidence of a corresponding viral infection, and is typically confirmed by the Western blot procedure. Detection of HIV virus by p24 antigen determination or detection of viral RNA by RT-PCR has been used to determine the amount of virus in circulation. Further, CD4/CD8 T cell ratios and other immune function tests are often used to monitor immune status and progression to AIDS. More recently, HIV tests using saliva or epithelia cells in the mouth have also been developed.

In view of the wide scope of individual diseases and the lack of reliable, rapid, and cost-effective diagnostic tests, there is a need for more effective exosome capture and detection methodologies for diagnosing disease conditions that are reliable, rapid, cost-effective and less invasive.

SUMMARY

In one aspect, a composition for exosome capture includes an anti-ALG6 antibody specifically binding a human alpha-1,3-glucosyltransferase (ALG6) peptide consisting essentially of the amino acid sequence of YEAQRHWQEIT (SEQ ID NO: 1). In one embodiment, the exosome capture antibody is a polyclonal anti-ALG6 antibody. In another embodiment, the exosome capture antibody is a monoclonal anti-ALG6 antibody. In another embodiment, the anti-ALG6 antibody is conjugated to a detectable label or binding moiety, such as biotin. In another embodiment, the composition includes an anti-ALG6 antibody attached to a solid substrate, such as a microtiter plate.

In another aspect, a kit for capturing exosomes and detecting disease associated biomarkers includes an antibody specifically binding to human ALG6 or mammalian homologs thereof, and at least one disease associated biomarker binding agent. The kit may further include a plurality of centrifuge filters having a pore size smaller than 90 nm. The antibody in the kit may be further attached to a solid substrate for capturing exosomes in situ. In addition, the kit may include one or more detectable labels, for detecting the presence of one or more biomarkers present in the exosomes.

In another aspect, a method for diagnosing a disease condition in a subject includes the steps of: (a) contacting a bodily fluid sample from the subject with the anti-ALG6 antibody under conditions suitable for binding the exosomes to the anti-ALG6 antibody to form bound exosome-anti-ALG6 complexes; (b) contacting the bound complexes with at least one disease-associated biomarker binding agent suitable for detecting at least one disease-associated biomarker present in the exosomes; and (c) determining whether the exosomes include at least one disease associated biomarker.

In some embodiments, the disease condition is a non-infectious disease. In other embodiments, the disease condition is an infectious disease condition caused by a microorganism. The infectious disease condition may be acute or chronic.

The presence of a disease-associated biomarker in the exosomes is indicative of the disease condition in the subject, whereas the absence of a disease-associated biomarker is indicative of the absence of the disease condition in the subject.

In some embodiments, the exosomes are first isolated or purified and then contacted with one or more disease-associated biomarker binding agents.

In other embodiments, the exosomes are interrogated for the presence of the disease associated biomarkers in exosomes bound to exosome capture agents immobilized on a solid substrate. Exosome capture agents may include antibodies and lectins.

In certain preferred embodiments, the anti-ALG6 antibodies are immobilized on a solid substrate, which is directly interrogated for the presence of the disease associated biomarkers present in the exosomes bound thereto.

In some embodiments, the presence, absence or expression level corresponding to a disease-associated biomarker in the exosome is detected at the protein level (e.g., by ELISA, Western blot, antibody microarray, etc.).

In other embodiments, the presence, absence or expression level of a disease-associated biomarkers in the exosomes (and/or their expression levels) is detected at the RNA level (e.g., by RT-PCR, QT-PCR, oligonucleotide array, etc.).

In some embodiments, the biomarker binding agents include a second antibody specific for the disease-associated biomarker. In certain embodiments, detection of a disease associated biomarker includes the step of contacting the second antibody with a labeled antibody specific for the second antibody.

In other embodiments, detection of a disease associated biomarker includes the step of binding captured exosome complexes with one or more nucleic acid probes.

In other embodiments, detection of a disease associated biomarker includes the step of binding captured exosome complexes with at least one pair of oligonucleotide primers for PCR.

In some embodiments, the bodily fluid sample includes blood or plasma.

In other embodiments, the bodily fluid sample includes urine.

In some embodiments, the disease-associated biomarker is a protein specific for human disease, such as cancer.

In other embodiments, the disease-associated biomarker is protein specific for a microbial pathogen. The microbial pathogen may be a bacterium, yeast, protozoan, or a virus.

In one embodiment, the microbial pathogen is a human immunodeficiency virus, such as HIV-1 or HIV-2.

In other embodiments, the microbial pathogen is a hepatitis virus, such as hepatitis A virus (HAV), hepatitis B virus (HBV), hepatitis C virus (HCV), hepatitis D virus (HDV) or hepatitis E virus (HEV).

In another aspect, a method for purifying exosomes, includes the steps of: (a) contacting a bodily fluid sample from a subject with an anti-ALG6 antibody under conditions suitable for binding exosomes in the bodily fluid sample to the anti-ALG6 antibody to form bound exosome-anti-ALG6 complexes; and (b) selectively recovering exosomes from the bound exosome-anti-ALG6 bound complexes.

In another aspect, a kit for capturing exosomes and detecting a disease-associated biomarker, comprises an anti-ALG6 antibody and at least one disease-associated biomarker binding agent.

DETAILED DESCRIPTION

Figure 1:
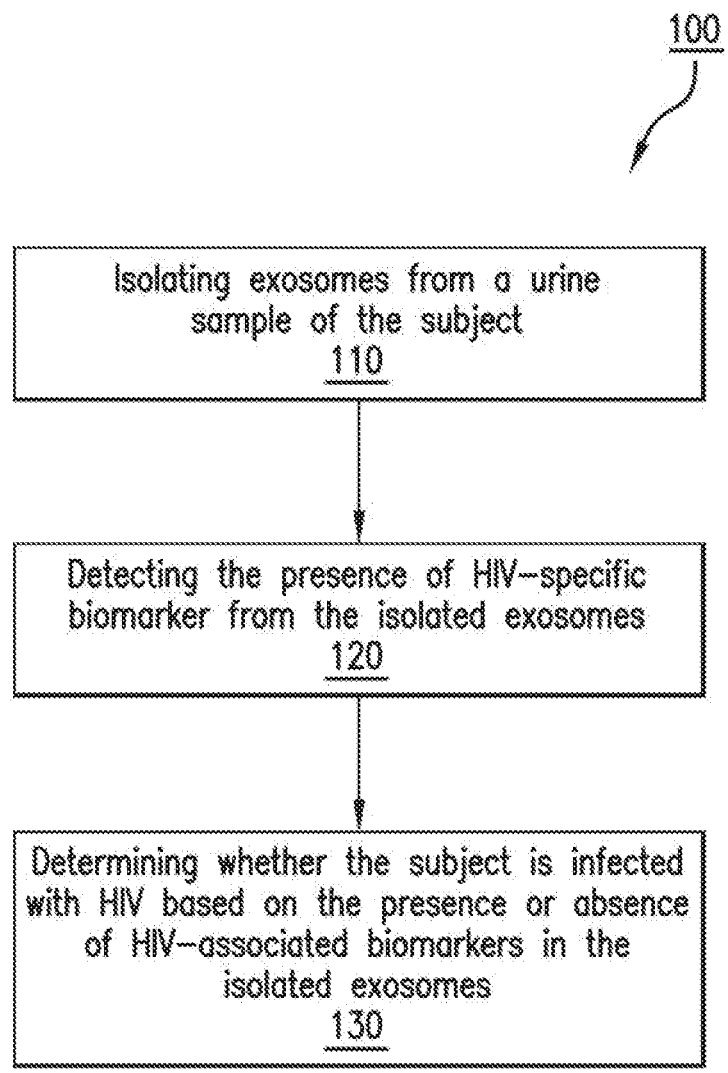
FIG. 1 is a flow chart showing an embodiment of an exemplary method for detecting HIV-infection or monitoring the progress of HIV-infection in a subject using a urine sample from the subject.
Figure 2A:
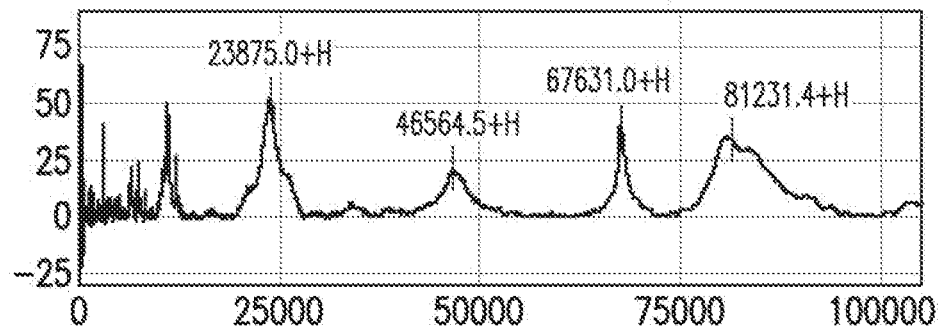
FIGS. 2A-2C are composites of samples SELDI-TOF-MS spectrum of urinary exosomes from patients in the HIVAN groups.
Figure 2B:
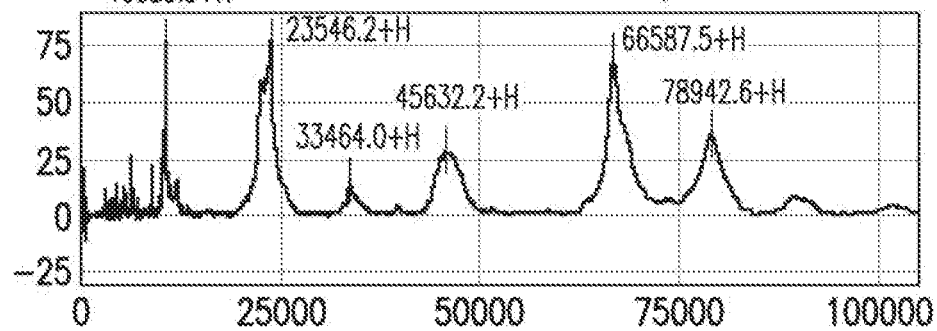
Figure 2C:
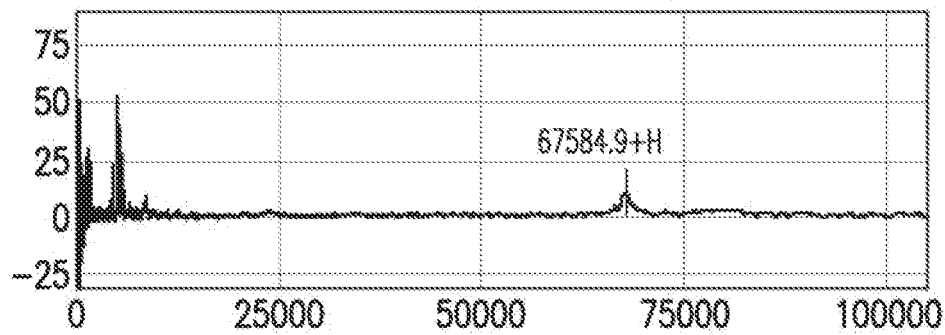
Figure 3A:
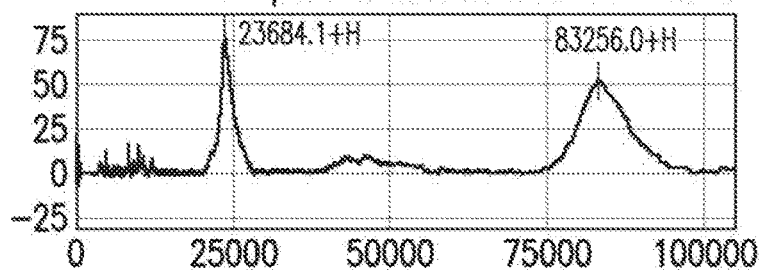
FIGS. 3A-3D are composites of samples SELDI-TOF-MS spectrum of urinary exosomes from patients in the African American (AA) HIV+ groups.
Figure 3B:
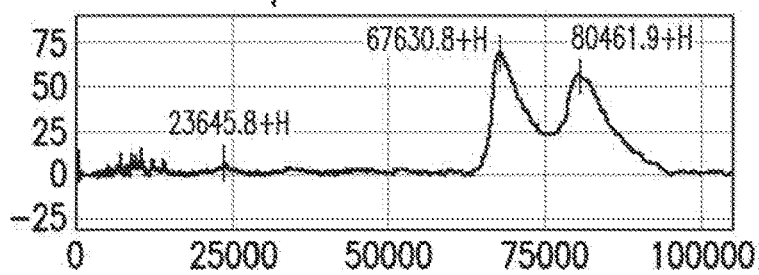
Figure 3C:
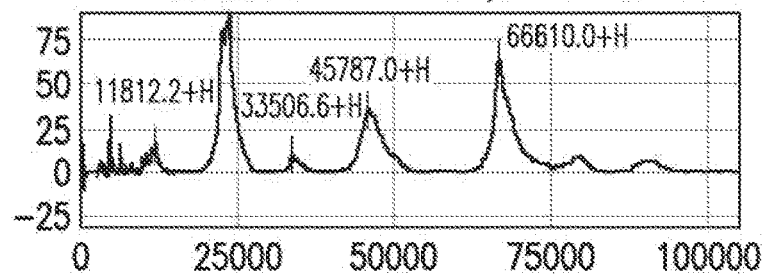
Figure 3D:
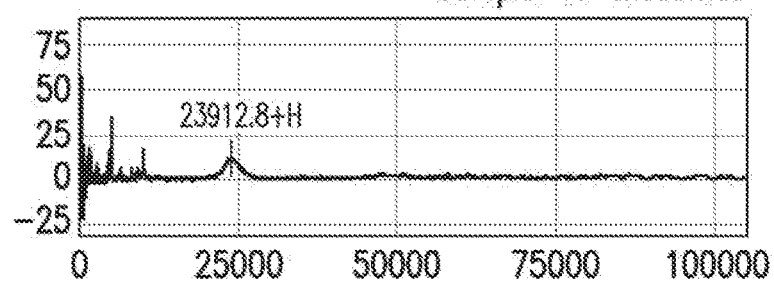
Figure 4A:
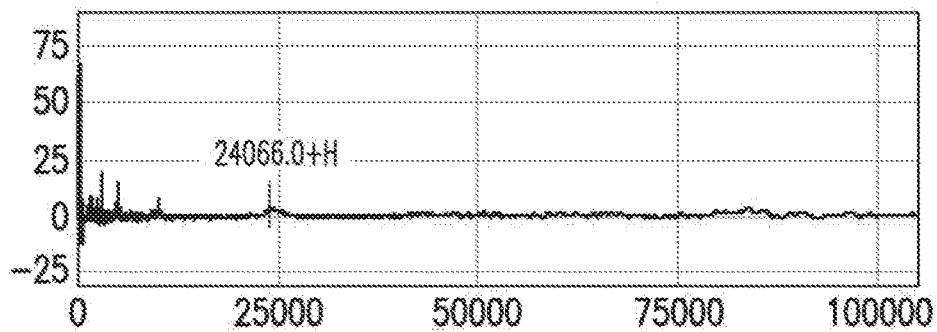
FIGS. 4A-4C are composites of samples SELDI-TOF-MS spectrum of urinary exosomes from patients in the HIV White groups.
Figure 4B:
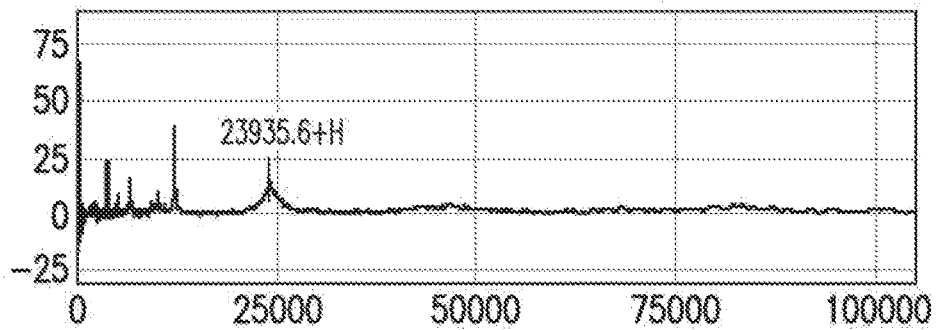
Figure 4C:
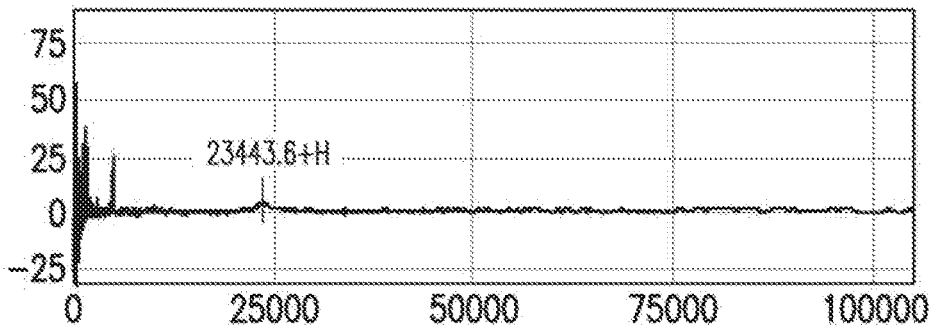
Figure 5A:
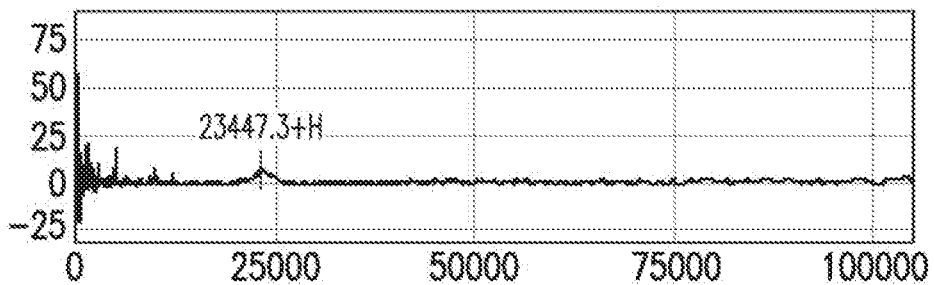
FIGS. 5A-5E are composites of samples SELDI-TOF-MS spectrum of urinary exosomes from patients in the FSGS groups.
Figure 5B:
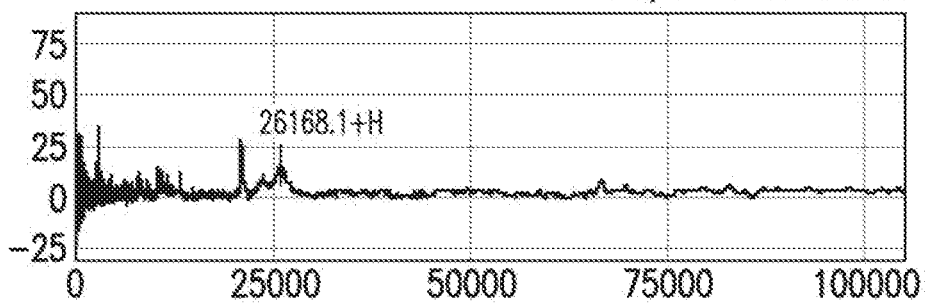
Figure 5C:
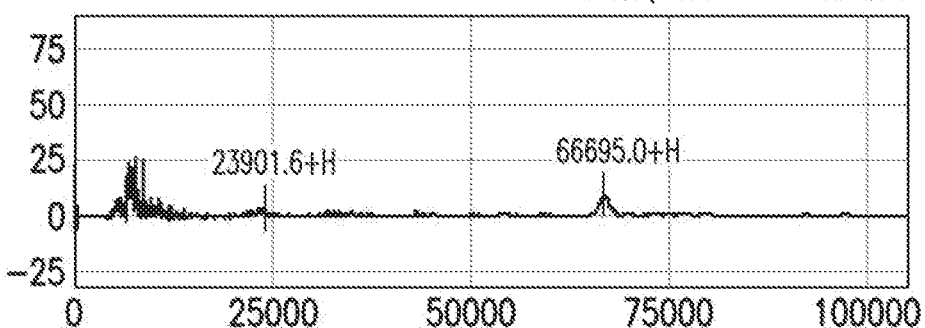
Figure 5D:
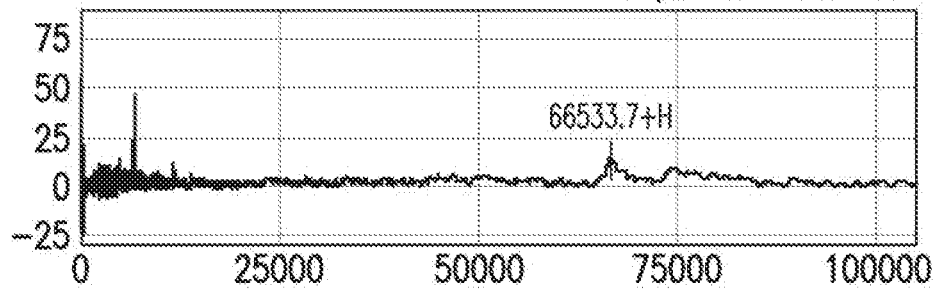
Figure 5E:
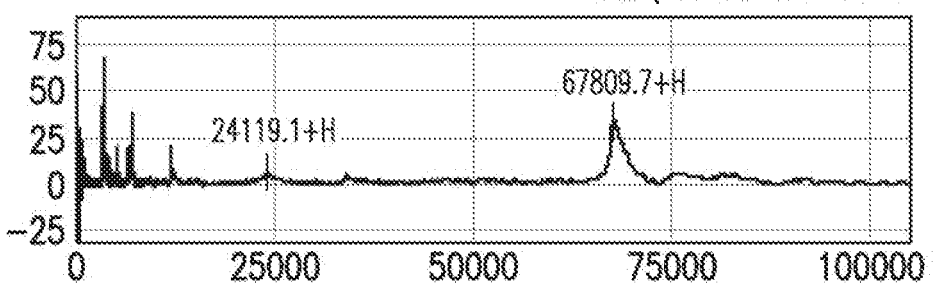
Figure 6A:
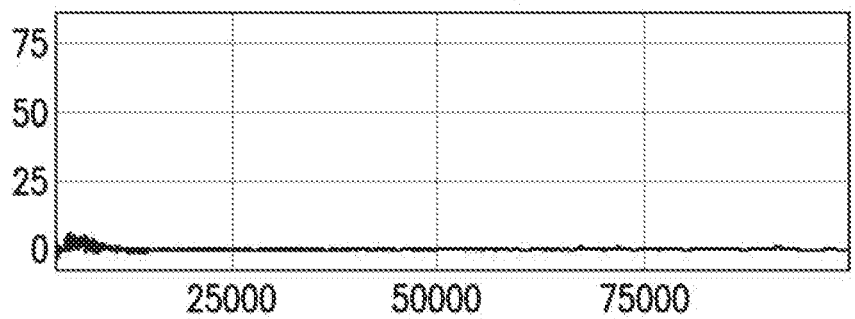
FIGS. 6A-6C are composites of samples SELDI-TOF-MS spectrum of urinary exosomes from patients in the Normal Controls groups.
Figure 6B:
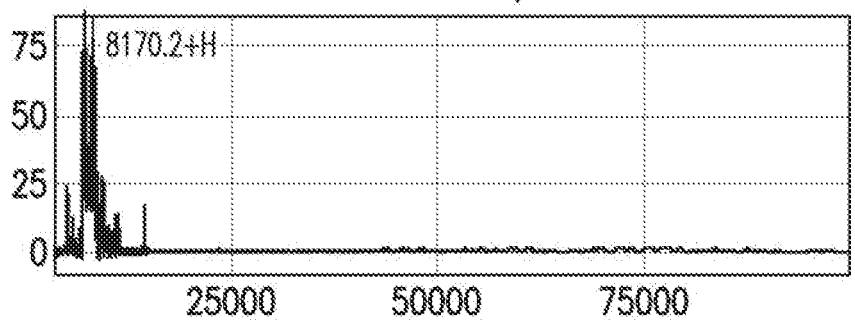
Figure 6C:
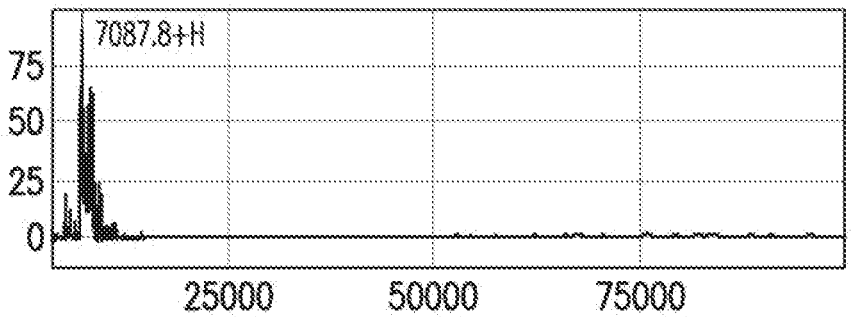
Figure 7A:
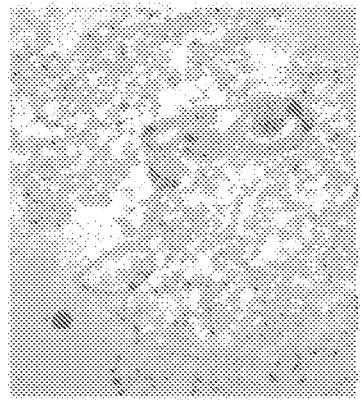
FIGS. 7A-7E are composites of transmission electron microscope (TEM) pictures of urinary exosomes isolated from patients from the HIVAN group (FIG. 7A), the FSGS group (FIG. 7B), the AA HIV+ group (FIG. 7C), the white HIV+ group (FIG. 7D), and the normal control group (FIG. 7E).
Figure 7B:
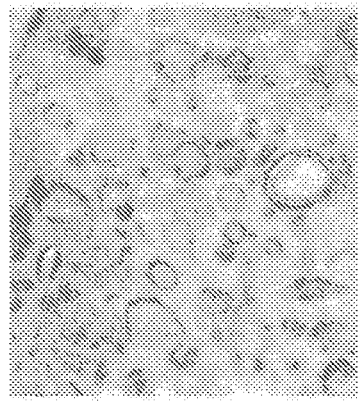
Figure 7C:
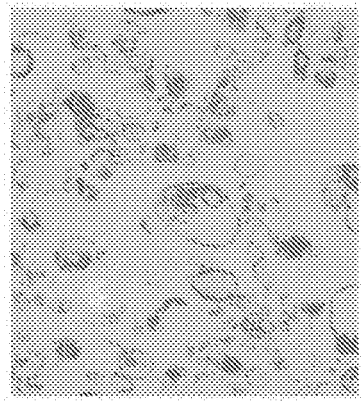
Figure 7D:
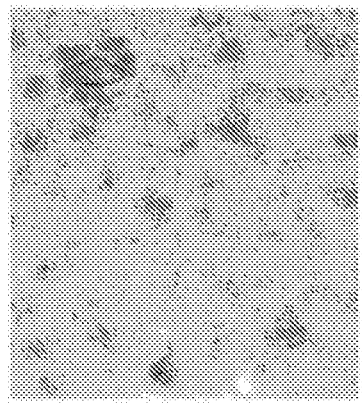
Figure 7E:
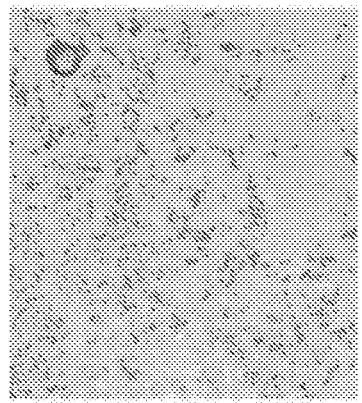

Herein incorporated by reference is the sequence listing filed with the USPTO as 1013-706 CONT.xml which was created on Mar. 9, 2023, and the size is 2,635 bytes.

The practice of the embodiments described in further detail below will employ, unless other wise indicated, conventional methods of diagnostics, molecular biology, cell biology, biochemistry and immunology within the skill of the art. Such techniques are explained fully in the literature. All publications, patents and patent applications cited herein, whether supra or infra, are hereby incorporated by reference in their entirety.

It is appreciated that certain features of the invention, which are for clarity described in the context of separate embodiments may also be provided in combination in a single embodiment. Conversely various features of the invention, which are for brevity, described in the context of a single embodiment, may also be provided separately and/or in any suitable sub-combination.

Definitions

As used herein, the following terms shall have the following meanings:

As used herein, the terms "biomarker" and "infectious agent-associated biomarker" are used interchangeably with reference to any molecular entity that can be used as an indicator of a disease, including an acute infectious disease or chronic infectious disease condition in an organism. The biomarker may be any detectable protein, nucleic acid, such as an mRNA or microRNA, lipid, or any product present and/or differentially expressed in exosomes present in bodily fluids following an infection and/or coincident with an infectious disease condition whose presence and/or concentration reflects the presence, severity, type or progression of an acute or chronic infection in a subject. In molecular terms, biomarkers may be detected and quantitated in a subject using genomics, proteomics technologies or imaging technologies.

An "infectious agent associated biomarker" or "virus-associated cellular biomarker" are used with reference to cellular biomarkers whose expression is altered in response to a disease associated (such as a virus) or infectious disease condition and whose differential expression relative to non-infected cells is diagnostic of an infection or disease caused by that particular infectious agent.

The term "antibodies" as used herein includes native antibodies, as well as any antibody derived fragment selected from the group consisting of: IgG, antibody variable region; isolated CDR region; single chain Fv molecule (scFv) comprising a VH and VL domain linked by a peptide linker allowing for association between the two domains to form an antigen binding site; bispecific scFv dimer; minibody comprising a scFv joined to a CH3 domain; diabody (dAb) fragment; single chain dAb fragment consisting of a VH or a VL domain; Fab fragment consisting of VL, VH, CL and CHI domains; Fab' fragment, which differs from a Fab fragment by the addition of a few residues at the carboxyl terminus of the heavy chain CHI domain, including one or more cysteines from the antibody hinge region; Fab'-SH fragment, a Fab' fragment in which the cysteine residue(s) of the constant domains bear a free thiol group; $F(ab')_2$, bivalent fragment comprising two linked Fab fragments; Fd fragment consisting of VH and CHI domains; derivatives thereof; and any other antibody fragment(s) retaining antigen-binding function. Fv, scFv, or diabody molecules may be stabilized by the incorporation of disulphide bridges linking the VH and VL domains. When using antibody-derived fragments, any or all of the targeting domains therein and/or Fc regions may be "humanized" using methodologies well known to those of skill in the art. In some embodiments, the infectious-agent associated antibody is modified to remove the Fc region.

As used herein, the term "specifically binding" refers to the interaction between binding pairs (e.g., an antibody and its target antigen or peptide, or between two nucleic acids), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.). In some embodiments, the interaction has an equilibrium dissociation constant (Kd) of at least $10^{-6}$ moles/liter, at least $10^{-7}$ moles/liter, at least $10^{-8}$ moles/liter or at least $10^{-9}$ moles/liter.

As used herein, the term "bodily fluid sample" refers to a sample of bodily fluid obtained from a mammal subject, preferably a human subject. Exemplary bodily fluid samples include urine, blood, saliva, serum, plasma, cyst fluid, pleural fluid, ascites fluid, peritoneal fluid, amniotic fluid, epididymal fluid, cerebrospinal fluid, bronchoalveolar lavage fluid, breast milk, tears, sputum, and combinations thereof. In a preferred embodiment, the bodily fluid sample is urine. Unless otherwise noted, as used herein, the terms "bodily fluid sample" and "sample" are to be considered synonymous with any of the above-described bodily fluid samples.

As used herein, a "detectable label" refers to a molecule, compound or a group of molecules and/or compounds associated with detection of a polypeptide biomarker or nucleic acid biomarker. Signals from the detectable label may be detected by various means depending on the nature of the detectable label. Detectable labels may include radioisotopes, fluorescent compounds (e.g., fluorescein, rhodamine, phycoerythrin, chemiluminescent compounds, bioluminescent compounds, nucleotide chromophores, substrates, enzymes (e.g., alkaline phosphatase, horseradish peroxidase, β-glactosidase, luciferase, green fluorescent protein (GFP), blue fluorescent protein (BFP)), enzyme substrates (e.g., fluorescent moieties or proteins, luminescent moieties (e.g., luciferin, aequorin, Evidot® quantum dots supplied by Evident Technologies, Troy, N.Y., or Qdot™ nanoparticles supplied by the Quantum Dot Corporation, Palo Alto, Calif.), colorimetric labels, such as colloidal gold, colored glass or plastic (e.g., polystyrene, polypropylene, and latex) beads and the like. Exemplary means for detecting a detectable label include but are not limited to spectroscopic, photochemical, biochemical, immunochemical, electrical, electromagnetic, radiochemical, optical or chemical means and combinations thereof, and may encompass fluorescence, chemifluorescence, chemiluminescence, electrochemiluminescence and the like. A detectable label can be attached or structurally incorporated into a detection antibody or a secondary antibody.

As used herein, a "biomarker profile" refers to one or more biomarkers diagnostic for a particular disease and/or infection. The biomarker profile may include biomarkers directly derived from a cellular gene or infectious agent gene, including those whose expression levels or profile is characteristic of an individual who has a disease or is acutely or chronically infected with a particular infectious agent. Accordingly, the step of determining whether the subject carries a disease associated biomarker may be based on detecting the presence, absence or differential expression of one or more disease-associated biomarkers present in the isolated exosomes. As used herein, the term "differential expression" refers to a qualitative and/or quantitative changes in biomarker expression levels relative to a control sample.

The term "increased level" refers to an expression level that is higher than a normal or control level customarily defined or used in the relevant art. For example, an increased level of immunostaining of an exosome preparation from a bodily fluid sample is a level of immunostaining that would be considered higher than the level of immunostaining of a control exosome preparation by a person of ordinary skill in the art. As used herein, the described biomarker may exhibit increased expression levels of at least 10%, at least 20%, at least 30%, at least 40%, at least 50%, at least 80%, at least 100%, at least 2-fold, at least 3-fold, at least 5-fold, at least 10-fold, at least 50-fold or at least 100-fold increase or more relative to a suitable reference level.

The term "decreased level" refers to an expression level that is lower than a normal or control level customarily defined or used in the relevant art. As used herein, the described biomarkers may exhibit decreased expression levels of at least at least 10%, at least 20%, at least 30%, at least 40%, at least 50%, at least 80%, at least 100%, at least 2-fold, at least 3-fold, at least 5-fold, at least 10-fold, at least 50-fold or at least 100-fold decrease or more relative to a suitable reference level.

The term "expression level of a disease-associated biomarker" may be measured at the transcription level, in which case the presence and/or the amount of a polynucleotide is determined, or at the translation level, in which case the presence and/or the amount of a polypeptide is determined.

The terms "gene product" and "expression product of a gene" refers to the transcriptional products of a gene, such as mRNAs and cDNAs encoded by the gene, and/or the translational products of a gene, such as peptides encoded by the gene, and fragments thereof.

The term "infectious disease condition" refers to a condition that is related to, or resulted from, an infectious disease. Further, the term "hepatitis disease conditions" include, but are not limited to, hepatitis, cirrhosis and hepatocellular carcinoma (HCC).

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

Compositions for Exosome Capture
1. Exosome Capture Agents

Human asparagine-linked glycosylation 6 homolog (ALG6) is an alpha-1,3-glucosyltransferase which catalyzes the addition of glucose residue to the lipid-linked oligosaccharide precursor for N-linked glycosylation. Although, the enzyme is localized to the endoplasmic reticulum of human cells, antibodies to an ALG6 peptide were unexpectedly found to exhibit unique exosome capture capabilities.

In one aspect, a composition for exosome capture comprising an anti-ALG6 antibody. The antibody may specifically bind to human ALG6 or other mammalian homologs thereof. In one embodiment, the anti-ALG6 antibody specifically binds a human ALG6 peptide consisting of the amino acid sequence of SEQ ID NO: 1. As such, the exosome capture antibody may be specifically raised against an immunogenic composition comprising a peptide consisting of the amino acid sequence in SEQ ID NO: 1. In some embodiments, the exosome capture antibody is a polyclonal anti-ALG6 antibody. In other embodiments, the exosome capture antibody is a monoclonal anti-ALG6 antibody. In another embodiment, an anti-ALG6 antibody directed against a synthetic peptide corresponding to a region within the N terminal amino acids 38-50 (GDYEAQRHWQEIT) (SEQ ID NO: 2) of Human ALG6 (alpha-1,3-glucosyltransferase).

In some embodiment, a detectable label or binding moiety, such as biotin, is conjugated or structurally incorporated into the anti-ALG6 antibody. The addition of binding moieties, such as biotin, can facilitate conjugation to other macromolecules, such as streptavidin-linked enzymes, such as streptavidin-HRP or streptavidin-linked secondary antibodies for detection of exosome biomarkers as further described below.

In other embodiments, the composition includes an anti-ALG6 antibody attached or immobilized onto a solid substrate, such as a microtiter plate, for capturing exosomes. This can allow for in situ interrogation disease associated biomarkers in exosomes bound to the solid substrate.

In some embodiments, two or more antibodies may be immobilized onto the solid substrate, each binding to different epitopes on an exosome protein and/or different exosome proteins. The antibodies may include both polyclonal antibodies and monoclonal antibodies and may include native immunoglobulin molecules, as well as fragments and/or combinations of those immunoglobulin molecules, including humanized versions of immunoglobulin molecules or fragments thereof, as long as they retain the ability to serve as exosome capture agents or detection agents for disease associated biomarkers.

In some cases, as an alternative to antibodies, lectins may be used alone or in combination with the anti-ALG6 antibodies. Lectins have a particular affinity for glycan markers, such as glycoproteins, which are often present in exosomes, including tumor cell-derived exosomes, such as hepatocellular carcinoma (HCC)-derived exosomes. Non-limiting examples of lectins for immobilization on a substrate include *Lens culinaris* agglutin (LCA), *Lens culinaris* lectin (LCH), *Galanthus nivalis* lectin (GNA), *Narcissus pseudonarcissus* lectin (NPL), *Allium sativum* lectin (ASA), *Sambucus nigra* lectin (SNA), *Maackia amurensis* lectin (MAL), Concanavalin A (Con A), *Aleuria aurantia* lectin (AAL), Lotus tetragonolobus lectin (LTL), *Naja mossambica* lectin (NML), *Dolichos biflorus* agglutinin (DBA), *Helix aspersa* lectin (HAL), *Psophocarpus tetragonolobus* lectin II (PTL II), *Wisteria floribunda* lectin (WFL), *Erythrina cristagalli* lectin (ECL), *Griffonia simplicifolia* lectin II (GSL II) and *Phaseolus vulgaris* leucoagglutinin (PHA-L).

In certain embodiments, exosomes are bound to a solid substrate with immobilized lectins binding high mannose structures, including 1,3- or 1,6-linked high mannose structures on the surface of exosomes. In one embodiment, *Galanthus nivalis* (GNA) lectins are bound to a solid substrate. GNA lectins can bind to 1,3 and 1,6-linked high mannose structures on the surface of exosomes.

AFP-L3, an isoform of alpha-fetoprotein, is the major glycoform in the serum of HCC patients and is known to bind LCA. For diagnosis of HCC, the AFP-L3 marker may be detected in combination with other AFP glycoforms, including AFP-P4, AFP-P5 (E-PHA), and monosialylated AFP. In contrast, the L1 isoform of AFP (AFP-L1) may be used to diagnose a non-HCC inflammation of liver disease condition. In certain preferred embodiments, LCA lectin is used to bind exosomes in bodily fluids from HCC subjects.

The solid substrate to which the capture antibody is bound may be any water-insoluble or water-insuspendable solid substrate. Exemplary solid substrates encompassed herein include microtiter plates made of plastics, such as polystyrene and polypropylene, those formed partially or entirely of glass (e.g., controlled pore glass), polysaccharides (e.g., agarose), polyacrylamides, silicones, plastics, such as polystyrene, polypropylene and polyvinyl alcohol, solid and semi-solid matrixes, such as aerogels and hydrogels, resins, beads, magnetic beads, biochips (including thin film coated biochips), nanoparticles, microfluidic chips, a silicon chips, multi-well plates (also referred to as micro-titer plates or microplates), membranes, filters, conducting and non-conducting metals, glass (including microscope slides) and magnetic supports, including magnetizable particles of cellulose or other polymers. Further examples of solid substrates include silica gels, polymeric membranes, particles, derivatized plastic films, glass beads, cotton, plastic beads, alumina gels, and polysaccharides such as Sepharose, nylon, latex bead, magnetic bead, paramagnetic bead, super-paramagnetic bead, starch and the like.

Exosome capture agents, including the ALG6 antibodies, may be bound to the solid substrate by covalent bonds or by adsorption. The capture agents may be attached using any crosslinking agents suitable for attachment of antibodies. Reagents included in the methods and kits described herein may be provided as reagents embedded, linked, connected, attached, placed or fused to any of the solid substrate materials described above.

In some embodiments, sample fluids may be passed through a centrifuge filter for isolating and concentrating exosomes prior to immobilization onto the solid substrate as further described below. This may further help to reduce non-specific binding of sample fluid components to the solid substrate.

Alternatively, exosomes may be purified by affinity (or column) chromatography using anti-ALG6 antibodies immobilized on a suitable column matrix, whereby a bodily fluids are loaded onto the column enabling exosomes to bind to the anti-ALG6 antibodies in a first step and then elute the exosomes bound to the column in a second step. The eluted exosomes may then be tested directly for biomarker binding or they may be applied to the above described solid substrate (i.e., a second solid substrate).

2. Disease Associated Biomarkers

In some embodiments, the biomarker is a protein. Where the biomarker is a protein, the disease associated biomarker binding agent is a detection antibody.

In other embodiments, the biomarker is a nucleic acid. Where the biomarker is a nucleic acid, the disease associated biomarker binding agent is a nucleic acid. Exemplary nucleic acids include both single-stranded and double-stranded polynucleotides or oligonucleotides of DNA or RNA. Exemplary nucleic acids include viral genomic DNAs or RNAs, including reverse transcribed derivatives thereof.

A. Non-Infectious Disease Biomarkers

In some embodiments, the disease-associated biomarker is a protein or nucleic acid specific for human disease, such as cancer. Exemplary cancers include prostate cancer, ovarian cancer, liver cancer, testicular cancer, pancreatic cancer, colon cancer and breast cancer. Exemplary cancer-specific biomarkers include prostate specific antigen (PSA), prostate specific membrane antigen (PSMA), early prostate cancer antigen-1 (EPCA-1), early prostate cancer antigen-2 (EPCA-2), CA-125, B-HGG, CA-19-9, carcioembryonic antigen (CEA), EGFR, KIT, ERB2, cathepsin D, human glandular kallikrein 2 (hK2), alpha-methylacyl coenzyme A racemase (AMACR), galectin-3, hepsin, macrophage inhibitory cytokine (MIC-1), and insulin-like growth factor binding protein 3 (IGFBP3).

In other embodiments, the disease-associated biomarker is a protein or nucleic acid specific for a non-cancerous disease, such as Alzheimer's disease (e.g., β-amyloid (AB), anti-AB antibodies, β-site APP-cleaving enzyme 1 (BACE1), soluble Aβ precursor protein (sAPP), beta-2 microglobulin (B2M), carcioembryonic antigen, cortisol, epidermal growth factor receptor, IGFBP2, IL-17, pancreatic polypeptide (PPY), and VCAM1); chronic traumatic encephalopathy (CTE) (e.g., cerebrospinal fluid p-tau); diabetes (e.g., adiponectin, leptin, ghrelin, resistin, autoantibodies to insulin, carboxypeptidase E, insulin degrading enzyme, autoantibodies to glutamic acid decarboxylase, autoantibodies to IL-2, autoantibodies to IA-2, incretins, TNF-α, and IL-6), and heart disease.

B. Infectious Agent and Infectious Agent-Associated Biomarkers

In other embodiments, the disease-associated biomarker is a protein or nucleic acid specific for an infectious agent, such as a microbial pathogen. The infectious agent may be a bacterium, yeast, protozoan, or a virus. Thus, an infectious agent biomarker may be a protein or nucleic acid encoded by a virus, bacteria, fungus, protozoan etc. The infectious agent biomarker may be directly derived from the infectious agent. Alternatively, the infectious agent biomarker may be a cellular biomarker product whose deregulated expression relative to non-infected cells is diagnostic of an infection or disease caused by that particular infectious agent.

In one embodiment, the infectious agent is a virus. In certain preferred embodiments, the virus human immunodeficiency virus (HIV) type 1 or type 2 (HIV-1 and HIV-2).

In another embodiment, the virus is a hepatitis virus selected from the group consisting of hepatitis A virus (HAV), hepatitis B virus (HBV), hepatitis C virus (HCV), hepatitis D virus (HDV) and hepatitis E virus (HEV).

Preferred infectious agent-associated biomarkers include, but are not limited to HIV (e.g., HIV-1, HIV-2)-associated biomarkers and hepatitis virus (e.g., hepatitis A virus (HAV), hepatitis B virus (HBV), hepatitis C virus (HCV), hepatitis D virus (HDV) and hepatitis E virus (HEV))-associated biomarkers. As used herein, the terms "HIV-associated biomarker" or "hepatitis virus-associated biomarker" refer to HIV or hepatitis virus proteins, nucleic acids or fragments thereof, as well as cellular biomarker products whose differential expression relative to non-infected cells is diagnostic of HIV or hepatitis virus infections.

In certain particular embodiments, the biomarker is an HIV-associated protein selected from the group consisting of Nef, gp120, protease, Vif, Gag-Pol, Gag, p24, Rev, reverse transcriptase (RT), Tat, p1, p17, Vpu, Vpr, gp41 and DNA polymerase.

In other embodiments the biomarker is a hepatitis virus biomarker associated with hepatitis A virus (HAV), hepatitis B virus (HBV), hepatitis C virus (HCV), hepatitis D virus (HDV) and/or hepatitis E virus (HEV). Any of the hepatitis virus proteins or nucleic acids described herein may be utilized as hepatitis virus biomarkers or hepatitis virus-associated biomarkers in accordance with the present application.

Hepatitis A virus (HAV) is a small, nonenveloped, spherical virus classified in the genus Hepatovirus of the Picornaviridae family. The HAV genome consists of a single-strand, linear, 7.5 kb RNA molecule encoding a polyprotein precursor that is processed to yield the structural proteins and enzymatic activities required for viral replication. HAV encodes four capsid proteins (A, B, C and D) which contain the major antigenic domains recognized by antibodies of infected individuals. In addition to the capsid proteins, antigenic domains have been reported in nonstructural proteins such as 2A and the viral encoded protease. Another important HAV antigenic domain has been described in the junction between the capsid precursor P1 and 2A. In some embodiments, the HAV polyproteins VP0, VP1, and VP3 (aka 1AB, 1D, and 1C, respectively) are used as HAV biomarkers.

Hepatitis B virus is an enveloped non-cytopathic double-stranded circular DNA virus. It is a member of the Hepadnaviridae family. The virus consists of a central core that contains a core antigen (HBcAg) surrounded by an envelope containing a surface protein/surface antigen (HBsAg) and is 42 nm in diameter. It also contains an e antigen (HBeAg) which, along with HBcAg and HBsAg, is helpful in identifying this disease. In HBV virions, the genome is found in an incomplete double-stranded form. Upon infection by HBV, the incomplete partial double stranded DNA is repaired to form a 3.2-kb covalently closed circular (ccc) DNA, which serves as a template to transcribe overlapping RNA species including a 3.5-kb pregenomic RNA coding for reverse-transcriptase (polymerase), core, PreS, S and X proteins. These RNAs are then translated into HBV proteins or reverse-transcribed into HBV DNA. All of the HBV proteins play important roles in HBV transcriptional regulation, viral package, reverse-transcription and viral DNA recycling.

Exemplary hepatitis B virus (HBV) biomarker proteins for use in present application include the HBV core antigen (HBcAg), HBV surface antigen (HBsAg), HBV e antigen (HBeAg), HBV X protein (HBx), HBV polymerase, and the HBV envelope proteins S, M, and L.

HCV is an RNA virus of the Flaviviridae, genus Hepacivirus, and is most closely related to the pestiviruses, BVDV and GBV-B. The HCV genome is composed of a single positive strand of RNA, approximately 9.6 kb in length. The HCV genome possesses a continuous, translational open reading frame (ORF) that encodes a polyprotein of about 3,000 amino acids. The structural protein(s) appear to be encoded in approximately the first quarter of the N-terminus region of the ORF, the remainder coding for non-structural proteins. The polyprotein serves as the precursor to at least 10 separate viral proteins critical for replication and assembly of progeny viral particles. The organization of structural and non-structural proteins in the HCV polyprotein is as follows: C-E1-E2-p7-NS2-NS3-NS4a-NS4b-NS5a-NS5b. Examples of HCV biomarkers include, but are not limited to, HCV core antigen (HCVcAg), HCV C protein, HCV E1 protein, HCV E2 protein, HCV p7 protein, HCV NS2 protein, HCV NS3 protein, HCV NS4a protein, HCV NS4b protein, HCV NS5a protein and HCV NS5b protein.

The hepatitis delta virus (HDV) is a satellite RNA virus dependent on hepatitis B surface antigens to assemble its envelope and form new virions to propagate infection. HDV has a small 1.7 Kb genome making it the smallest known human virus. The HDV virion is composed of a ribonucleoprotein core and an envelope. The core contains HDV-RNA, and hepatitis delta antigen (HDAg), which is the only protein encoded by this virus. The envelope is formed by the surface antigen protein (hepatitis B surface antigen, or HBsAg) of the helper virus, hepatitis B. The envelope is the sole helper function provided by HBV. HDV is able to replicate its RNA within cells in the absence of HBV, but requires HBsAg for packaging and release of HDV virions, as well as for infectivity. As a result of the dependence of HDV on HBV, HDV infects individuals only in association with HBV.

Hepatitis E virus (HEV) is the causative agent of hepatitis E, a form of acute viral hepatitis that is endemic to many resource-limited regions of the world. It is estimated that about 2 billion people, which is about a third of the world population, live in areas endemic for HEV and are at risk for infection. In these areas, hepatitis E is the major form of acute hepatitis; in India for example about 50% of acute hepatitis is due to HEV.

HEV is a small non-enveloped virus with a size of 27-34 nm and is classified as a Hepevirus in the family Hepeviridae. The HEV genome is a single-stranded RNA of ~ 7.2 kb that is positive-sense, with a 5'-methylguanine cap and a 3' poly (A) stretch, and contains three partially overlapping open reading frames (ORFs)-called orf1, orf2 and orf3. HEV orf1, a polyprotein of 1693 amino acids, encodes the viral nonstructural functions. Functional domains identified in the HEV nonstructural polyprotein include (starting from the N-terminal end)-methyltransferase (MeT), papain-like cysteine protease (PCP), RNA helicase (Hel) and RNA dependent RNA polymerase (RdRp). HEV orf2 encodes a viral capsid protein of 660 amino acids, which is believed to encapsidate the viral RNA genome. HEV orf3 is believed to express a 114 amino acid protein that is dispensable for replication in vitro and is believed to function as a viral accessory protein, likely affecting the host response to infection.

Exemplary hepatitis viral nucleic acid sequences include, but are not limited to, nucleic acid sequences involved in transcription and translation (e.g., En1, En2, X, P) and nucleic acid sequences encoding structural proteins (e.g., core proteins including C and C-related proteins, capsid and envelope proteins including S, M, and/or L proteins, or fragments thereof) (see, e.g., FIELDS VIROLOGY, 2001, supra). Exemplary hepatitis C nucleic acid sequences include, but are not limited to, serine proteases (e.g., NS3/NS4), helicases (e.g., NS3), polymerases (e.g., NS5B), and envelope proteins (e.g., E1, E2, and p7). Hepatitis A nucleic acid sequences are set forth in, e.g., Genbank Accession No. NC_001489; hepatitis B nucleic acid sequences are set forth in, e.g., Genbank Accession No. NC_003977; hepatitis C nucleic acid sequences are set forth in, e.g., Genbank Accession No. NC_004102; hepatitis D nucleic acid sequence are set forth in, e.g., Genbank Accession No. NC_001653; hepatitis E nucleic acid sequences are set forth in, e.g., Genbank Accession No. NC_001434; and hepatitis G nucleic acid sequences are set forth in, e.g., Genbank Accession No. NC_001710.

In addition to the HIV and hepatitis viruses, additional viruses include, but are not limited to, human T-cell lymphotropic virus (HTLV) type I and type II (HTLV-I and HTLV-II), parvovirus B19 virus, transfusion transmitted virus (TTV); measles virus; rotaviruses, including Types A, B, C, D, and E; herpesviruses, including Epstein-Barr virus, human cytomegalovirus type 1 (HCMV-1), herpes simplex virus (HSV) types 1 and 2 (HSV-1 and HSV-2), human herpes virus type 6 (HHV-6), human herpes virus type 7 (HHV-7), human herpes virus type 8 (HHV-8); human papilloma virus (HPV) and its many serotypes; influenza type A viruses, including subtypes H1N1 and H5N1; severe acute respiratory syndrome (SARS) coronavirus; and other miscellaneous RNA viruses, including Arenaviridae (e.g., Lassa fever virus (LFV)), Filoviridae (e.g., Ebola virus (EBOV) and Marburg virus (MBGV)); Bunyaviridae (e.g., Rift Valley fever virus (RVFV) and Crimean-Congo hemorrhagic fever virus (CCHFV); and Flaviviridae, including West Nile virus (WNV), Dengue fever virus (DENV), yellow fever virus (YFV), and GB virus C (GBV-C), formerly known as Hepatitis G virus (HGV).

Exemplary bacteria include, but are not limited to *Mycobacterium* species, including *M. tuberculosis; Staphylococcus* species, including *S. epidermidis, S. aureus*, and methicillin-resistant *S. aureus; Streptococcus* species, including *S. pneumoniae, S. pyogenes, S. mutans, S. agalactiae, S. equi, S. canis, S. bovis, S. equinus, S. anginosus, S. sanguis, S. salivarius, S. mitis*; other pathogenic Streptococcal species, including *Enterococcus* species, such as *E. faecalis* and *E. faecium; Haemophilus influenzae, Pseudomonas* species, including *P. aeruginosa, P. pseudomallei*, and *P. mallei; Salmonella* species, including *S. enterocolitis, S. typhimurium, S. enteritidis, S. bongori*, and *S. choleraesuis; Shigella* species, including *S. flexneri, S. sonnei, S. dysenteriae*, and *S. boydii; Brucella* species, including *B. melitensis, B. suis, B. abortus*, and *B. pertussis; Neisseria* species, including *N. meningitidis* and *N. gonorrhoeae; Escherichia coli*, including enterotoxigenic *E. coli* (ETEC); *Vibrio cholerae, Helicobacter pylori, Chlamydia trachomatis, Clostridium difficile, Cryptococcus neoformans, Moraxella* species, including *M. catarrhalis, Campylobacter* species, including

*C. jejuni; Corynebacterium* species, including *C. diphtheriae, C. ulcerans, C. pseudotuberculosis, C. pseudodiphtheriticum, C. urealyticum, C. hemolyticum, C. equi; Listeria monocytogenes, Nocardia asteroides, Bacteroides* species, *Actinomycetes* species, *Treponema pallidum, Leptospirosa* species, *Klebsiella pneumoniae; Proteus* sp., including *Proteus vulgaris; Serratia* species, *Acinetobacter, Yersinia* species, including *Y. pestis* and *Y. pseudotuberculosis; Francisella tularensis, Enterobacter* species, *Bacteroides* species, *Legionella* species, *Borrelia burgdorferi*, and the like.

Exemplary fungi include, but are not limited to, *Aspergillus* species, Dermatophytes, *Blastomyces derinatitidis, Candida* species, including *C. albicans* and *C. krusei; Malassezia furfur, Exophiala werneckii, Piedraia hortai, Trichosporon beigelii, Pseudallescheria boydii, Madurella grisea, Histoplasma capsulatum, Sporothrix schenckii, Histoplasma capsulatum, Tinea* species, including *T. versicolor, T. pedis T. unguium, T. cruris, T. capitus, T. corporis, T. barbae; Trichophyton* species, including *T. rubrum, T. interdigitale, T. tonsurans, T. violaceum, T. yaoundei, T. schoenleinii, T. megninii, T. soudanense, T. equinum, T. erinacei*, and *T. verrucosum; Mycoplasma genitalia; Microsporum* species, including *M. audouini, M. ferrugineum, M. canis, M. nanum, M. distortum, M. gypseum, M. fulvum*, and the like.

Exemplary protozoans include, but are not limited to *Plasmodium* species, including *P. falciparum, P. vivax, P. ovale*, and *P. malariae; Leishmania* species, including *L. major, L. tropica, L. donovani, L. infantum, L. chagasi, L. mexicana, L. panamensis, L. braziliensis* and *L. guyanensi; Cryptosporidium, Isospora belli, Toxoplasma gondii, Trichomonas vaginalis*, and *Cyclospora* species.

An additional infectious agent includes the protease-resistant form of the prion protein (PrP), named scrapie disease associated prion protein (PrPSc), which is associated with a group of fatal neurodegenerative infectious pathologies, including the Creutzfeldt-Jakob disease (CJD), and is known to be associated with exosomes.

In certain embodiments, the infectious disease or infectious disease condition affects the kidney, such as pyelonephritis. In certain preferred embodiments, the infectious disease related condition is HIV-associated nephropathy (HIVAN).

In other embodiments, the infectious disease or infectious disease condition affects the liver, such as hepatitis, cirrhosis and hepatocellular carcinoma (HCC).

C. Liver Disease Associated Biomarkers

There are a number of markers that may be used individually or in combination for diagnosis of liver diseases, such as hepatitis, hepatic fibrosis and hepatocellular carcinoma. Exemplary liver disease markers include, but are not limited to CD10, CD26, CD81, AST, ALT, α-fetoprotein (AFP) and its various isoforms, including AFP-L1, AFP-L2, AFP-L3, AFP-P4, AFP-P5 (E-PHA), and monosialylated AFP; des-carboxyprothrombin (DCP), α-l-fucosidase (AFU), γ-glutamyl transferase, glypican-3 (GPC-3), squamous cell carcinoma antigen (SCCA), golgi protein 73 (GP73) and mucin 1 (MUC-1), 14-3-3 gamma, alpha-l-fucosidase, gamma-glutamyl transferase, glypican-3, squamous cell carcinoma antigen, protein C (PROC), retinal binding protein 4 (RBP4), alpha-1-B glycoprotein (A1BG), alpha-1-acid glycoprotein (AGP), Mac-2-binding protein (M2BP), complement Factor H (CFH), insulin-like growth factor binding protein acid labeled subunit (IGFALS).

In certain embodiments, an increased level of A1BG or a decreased level of CFH or IGFALS is/are indicative of the incidence and/or severity of acute or chronic hepatitis. In other embodiments, decreasing levels of protein C (PROC) and/or retinal binding protein 4 (RBP4) are indicative of the increasing severity of fibrosis.

Exosome biomarkers associated with renal tissues and renal diseases are of particular interest in view of being derived from renal epithelial cells and their ready detection in exosomes isolated from urine. Exemplary exosome biomarkers from normal urine include apical transporters present in each renal tubule segment, including the proximal tubule (sodium-hydrogen exchanger 3, sodium-glucose co-transporter 1 and 2, and aquaporin-1 (AQP1)), the thick ascending limb (sodium-potassium-chloride co-transporter 2 (NKCC2)), the distal convoluted tubule (thiazide-sensitive Na—Cl co-transporter (NCC)), and connecting tubule/collecting duct (AQP2, rhesus blood group C glycoprotein (RhCG, an ammonia channel), B1 subunit of vacuolar H+-ATPase, and pendrin); hepatocyte growth factor-regulated tyrosine kinase substrate, tumor susceptibility gene 101, vacuolar protein sorting 28 isoform 1, vacuolar protein sorting 28 isoform 2, vacuolar protein sorting 37B, vacuolar protein sorting 37C, EAP25, EAP45, EAP30, CHMP2A, CHMP2B, CHMP3, CHMP4B, CHMP5, CHMP1A, CHMP1B, CHMP6, vacuolar protein sorting factor 4A, and vacuolar protein sorting factor 4B. A database of urinary exosome proteins (and their sequences) from healthy human volunteers based on published and unpublished protein mass spectrometry data from the NHLBI Laboratory of Kidney and Electrolyte Metabolism is publicly available at http://dir.nhlbi.nih.gov/papers/lkem/exosome/.

D. Cellular Exosome Biomarkers

Because of their cellular origin, exosomes bear specific protein markers of the endosomal pathway, such as tetraspanins (CD63, CD9 and CD81), heat shock proteins (HSP70) and proteins from the Rab family (e.g., Rab5), Tsg101 and Alix, which are not found in other types of vesicles of similar size. The composition of exosomes is also known to reflect the particular cell types from which they are derived. Accordingly, exosome profiling using cellular exosome markers can provide information correlating the presence of infectious agent biomarkers or infectious agent associated cellular biomarkers with particular cell types in the context of diagnosing a disease.

Cellular exosome markers can provide useful internal controls for determining expression level changes relative to reference samples and can provide useful markers helpful in diagnosing phenotypic tissue changes, including e.g., liver damage, liver fibrosis, inflammation, hepatocellular carcinoma etc. Non-limiting examples of cellular exosome markers includes CD9, CD10, CD26, CD53, CD63, CD81, CD82, Rab5, Alix, TSG101, Hsc70 and Hsp90.

In addition, these cellular exosome surface markers can provide additional capture agents for detection of biomarkers in exosomes. In certain embodiments, a plurality of antibody capture agents may additionally immobilize cellular exosome markers described herein onto the solid substrate (in addition to e.g., ALG6) for capturing exosomes.

In other embodiments, cellular exosome markers reflecting tissue damage and/or disease exclusively associated with a particular disease state, such as hepatic fibrosis or hepatocellular carcinoma may be detected. In other embodiments, the cellular exosome markers may be increased relative to reference control samples or decreased relative to reference control cells. The increases or decreases may be evident in terms of total expression levels in an exosome preparation as a whole. Alternatively, the expression level changes may be evident in the total number of exosomes that are positive or negative for a particular marker.

Both types of liver epithelia (i.e., hepatocytes and cholangiocytes), natural killer T (NKT) cells, hepatic stellate cells, adult liver stem cells, and hepatic sinusoidal endothelial cells are exosome-releasing and/or exosome-targeting cells. Exosome biomarkers associated with hepatic tissues and liver diseases are of particular interest, because their markers can shed light in the incidence of prognosis of hepatitis-related conditions, including hepatocellular carcinoma (HCC).

Like other cell-derived exosomes, hepatic-derived exosomes include typical exosome markers, which may be utilized in the present application. These include common "marker" proteins, such as tetraspanins (e.g., CD9, CD10, CD26, CD53, CD63, CD81, CD82); endosome-associated proteins that are involved in MVB biogenesis, such as Alix and TSG101; cytoplasmic heat shock proteins, such as Hsc70 and Hsp90; and hepatic cell-type specific proteins and nucleic acids, including mRNAs, microRNAs (miRNAs) and other non-coding RNAs, the composition of which depends on the functional state of the cells (e.g., rested, stimulated, stressed, transformed, etc.).

E. Biomarker Panels

In certain embodiments, a biomarker panel of at least 2, 3, 4, 5, 10, 15, 20, 25, 30, 40 or 50 disease markers in a microarray may be employed. In certain embodiments, the biomarker panel assays expression of biomarker proteins. In other embodiments, the biomarker panel includes nucleic probes which assay for expression of biomarker mRNAs or miRNAs.

For example, biomarkers associated with a given disease or infection may be detected using a biomarker microarray panel containing immobilized biomarker-specific antibodies on a solid substrate. The microarray can be used in a "sandwich" assay as described above.

Typically, a microarray assay contains multiple incubation steps, including incubation with the samples and incubation with various reagents (e.g., primary antibodies, secondary antibodies, reporting reagents, etc.). Repeated washes are also needed between the incubation steps. In one embodiment, the microarray assays is performed in a fast assay mode that requires only one or two incubations. It is also conceivable that the formation of a detectable immune complex (e.g., a captured infectious agent-associated biomarker/anti-marker antibody/label complex) may be achieved in a single incubation step by exposing the biomarker microarray to a mixture of the sample and all the necessary reagents. In one embodiment, the primary and secondary antibodies are the same antibody.

In another embodiment, the biomarker microarray provides a competitive immunoassay. Briefly, a microarray comprising immobilized anti-marker antibodies is incubated with a test sample in the presence of a labeled infectious agent-associated biomarker standard. The labeled infectious agent-associated biomarker competes with the unlabeled infectious agent-associated biomarker in the test sample for the binding to the immobilized antigen-specific antibody. In such a competitive setting, an increased concentration of the specific infectious agent-associated biomarker in the test sample would lead to a decreased binding of the labeled infectious agent-associated biomarker standard to the immobilized antibody and hence a reduced signal intensity from the label.

A biomarker microarray panel can be processed in manual, semi-automatic or automatic modes. Manual mode refers to manual operations for all assay steps including reagent and sample delivery onto microarrays, sample incubation and microarray washing. Semi-automatic modes refer to manual operation for sample and reagent delivery onto microarray, while incubation and washing steps operate automatically. In an automatic mode, three steps (sample/reagent delivery, incubation and washing) can be controlled by a computer or an integrated breadboard unit with a keypad. For example, the microarray can be processed with a ProteinArray Workstation (PerkinElmer Life Sciences, Boston, Mass.) or Assay 1200™. Workstation (Zyomyx, Hayward, Calif.). Scanners by fluorescence, colorimetric and chemiluminescence, can be used to detect microarray signals and capture microarray images. Quantitation of microarray-based assays can also be achieved by other means, such as mass spectrometry and surface plasma resonance. Captured microarray images can be analyzed by stand-alone image analysis software or with image acquisition and analysis software package. For example, quantification of an antigen microarray can be achieved with a fluorescent PMT-based scanner—ScanArray 3000 (General Scanning, Watertown, Mass.) or colorimetric CCD-based scanner—VisionSpot (Allied Biotech, Ijamsville, Md.). Typically, the image analysis would include data acquisition and preparation of assay report with separate software packages. To speed up the whole assay process from capturing an image to generating an assay report, all the analytical steps including image capture, image analysis, and report generation, can be confined in and/or controlled by one software package. Such an unified control system would provide the image analysis and the generation of assay report in a user-friendly manner.

3. Detection Antibodies

Following the binding of the exosomes to the exosome capture agents, the exosomes may be interrogated for the presence of one or more disease-associated biomarker proteins using one or more detection antibodies for binding captured exosomes.

In certain embodiments, the detection antibody is specific for a disease associated biomarker. To facilitate detection of biomarkers in the exosomes, detection antibodies are labeled directly or indirectly with detectable label. The detection antibody itself may be linked to a detectable label directly, or it may be further contacted with a secondary binding agent containing the detectable label. In addition, a "direct label" (which is directly detectable) may be incorporated in the detection antibody directly or it may be incorporated in the secondary binding agent. Exemplary direct labels include fluorescent or luminescent tags, metals, dyes, radionuclides, and the like.

The presence, absence and/or biomarker expression level may be monitored directly or indirectly. Exemplary detection labels include enzymes, which can catalyze color or light emitting (luminescence) reactions, such as alkaline phosphatase, horseradish peroxidase and green fluorescent protein.

Means of detecting such labels are well known to those of skill in the art. Thus, for example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label.

Enzymes which can be used to label the antibody include, but are not limited to peroxidases, such as horseradish peroxidase, phosphatases, such as alkaline phosphatase, galactosidases, such as β-galactosidase, cholinesterases, such as acetylcholinesterase, glucorinidases, malate dehydrogenase, staphylococcal nuclease, delta-5-steroid isomerase, yeast alcohol dehydrogenase, alpha-glycerophosphate dehydrogenase, triose phosphate isomerase, asparaginase, glucose oxidase, ribonuclease, urease, catalase, glucose-6-phosphate dehydrogenase, glucoamylase or any other enzyme which can be conjugated to an antibody and its reaction with a substrate, measured (or detected).

Where the detectable label is an enzyme, addition of a chemical substrate of the enzyme allows for the development of a spectrophotometrically detectable reaction product indicative of the presence of the biomarker in the exosome sample. When exposed to an appropriate substrate, the enzyme can react with its corresponding substrate to produce a chemical reaction product which can be detected, for example, by colorimetric, chemiluminescent, fluorometric, electrochemiluminescent (ECL) or visual means.

In addition, a capture antibody or detection antibody may further include binding moieties for facilitating conjugation to other macromolecules, such as biotin for binding streptavidin etc. For example, detection antibodies can be labeled with biotin (i.e., biotinylated) to enable binding to various secondary binding agents, including enzyme conjugates, such as streptavidin-HRP).

Exemplary secondary binding agents include secondary antibodies and enzyme conjugates (e.g., streptavidin-linked enzyme conjugates, such as streptavidin-HRP) that can specifically bind to biotinylated detection antibodies. A secondary antibody is typically generated in a different species than the detection antibody (i.e., if the detection antibody is a rabbit antibody, the secondary antibody may be e.g., an anti-rabbit IgG antibody from goat, chicken, etc., but not rabbit). In this way, the secondary antibody can bind an IgG corresponding to the detection antibody.

In one embodiment, detection of a disease associated biomarker includes the step of contacting immobilized exosomes with a detection antibody directly. Thus, when incorporating a detectable label in the form of a fluorophore, radionuclide or other direct label into the detection antibody, the detectable label may be directly detected without inclusion of enzymatic substrates. For example, in certain preferred embodiments, the detection antibody is biotinylated and labeled with a streptavidin-fluorophore conjugate.

In another embodiment, detection of a disease associated biomarker includes the step of contacting immobilized exosomes with a secondary binding agent targeting a portion of the detection antibody for binding (e.g., the constant region of the detection antibody or biotin).

In either case, the detectable label in the detection antibody or in the secondary antibody provides a marker indicating the presence of a disease associated biomarker in the exosome. The binding affinity for the biomarker protein is usually the main determinant of immunoassay sensitivity. As the protein concentration increases the amount of binding agent bound increases leading to a higher measured response. A standard curve from a sandwich-binding assay has a positive slope. To quantify the extent of binding, control reporters and/or substrates can be included in the analysis.

4. Nucleic Acid-Based Detection Agents

In addition to protein-based biomarker detection, nucleic acid-based detection agents may be used for detecting any of the biomarker proteins described herein or other nucleic acids described herein. In some embodiments, the biomarker is a DNA, messenger RNA (mRNA), microRNA (miRNA) or a viral-induced miRNA. Both mRNAs and miRNAs are known to be shuttled through exosomes. MicroRNAs are small non-coding RNAs responsible of post-transcriptional regulation of gene expression through interaction with messenger RNAs (mRNAs). They are involved in important biological processes and are often dysregulated in a variety of diseases, including cancer and infections. Viruses also encode their own miRNAs, which can be loaded into RNA-induced silencing complexes (RISC) for gene silencing of host's genes and/or their own via blocking mRNA translation and/or initiating mRNA decay.

Exemplary HIV-1-associated miRNAs include hiv1-mir-H1 and hiv-1-miR-N367.

Exemplary hepatitis-associated miRNAs include miR-122 and mrR-199.

In the past few years evidence of the presence of cellular miRNAs in extracellular human body fluids such as serum, plasma, saliva, and urine has accumulated, including their cofractionation (or colocalization) with exosomes.

miRNA markers for liver disease, such as liver fibrosis include miR-92a, miR-122, miR-148a, miR-194, miR-155, miR-483-5p and miR-671-5p, which exhibit progressive increases at higher fibrotic stages and miR-106b, miR-1274a, miR-130b, miR-140-3p, miR-151-3p, miR-181a, miR-19b, miR-21, miR-24, miR-375, miR-5481, miR-93, and miR-941, which exhibit progressive decreases in expression at higher fibrotic stages.

HCC cell-derived exosomes are known to contain an enriched fraction of miRNAs. Exemplary HCC-associated miRNAs include, but are not limited to miRNA-1, miRNA-122, miR-584, miR-517c, miR-378, miR-520f, miR-142-5p, miR-451, miR-518d, miR-215, miR-376a, miR-133b, miR-367. In certain embodiments, a panel of diagnostic markers includes one or more miRNAs of the miR-17-92 cluster, which are known to be transactivated by c-Myc, such as miR-17-5p, miR-18a, miR-19a, miR-19b, miR-20a and miR-92a-1.

In certain embodiments, the biomarker binding agents include one or more oligonucleotide probes for reverse transcriptase polymerase chain reaction (RT-PCR) amplification of RNAs in the exosomes, including mRNAs, miRNAs and the like.

Probe-target hybridization may be detected and quantified by fluorescence-based detection of fluorophore-labeled targets to determine relative abundance of nucleic acid sequences in the target. The oligonucleotide probes may be attached to any of the above described solid substrates by e.g., covalent bonding to a chemical matrix (via epoxy-silane, amino-silane, lysine, polyacrylamide or others). The solid surface can be glass or a silicon chip or microscopic beads.

Kits

In another aspect, a kit for capturing or purifying exosomes from bodily fluids, diagnosing diseases or monitoring the progress of diseases in a subject includes an antibody specifically directed against human ALG6 and one or more disease associated biomarker binding agents. The antibody in the kit may be further attached to a solid substrate for capturing exosomes in situ as described above. In some embodiments, the one or more disease associated biomarker binding agents are attached to a solid substrate. In some embodiments, the kit includes an antibody specifically directed against a peptide comprising the amino acid sequence of SEQ ID NO: 1 and one or more disease associated biomarker binding agents. In some embodiments, the kit includes an antibody specifically directed against a peptide consisting of the amino acid sequence of SEQ ID NO: 1 and one or more disease associated biomarker binding agents.

In certain embodiments, the kit may further include one or more centrifuge filters for capturing the exosomes. In one embodiment, one or more of the centrifuge filters have a pore size smaller than 90 nm. In another embodiment, one or more of the centrifuge filters may have a molecular weight cutoff of 500 kd-50 kd. In another embodiment, one or more of the centrifuge filters have a molecular weight cutoff of 100 kd.

Alternatively, or in addition, the anti-ALG6 antibodies can be used as a capture agent for exosomes by immunoaffinity chromatography, wherein anti-ALG6 antibodies are loaded onto a suitable antibody binding matrix (e.g., Protein A-Sepharose) for subsequent loading of bodily fluids to the column so that exosomes bind to the antibodies in a first step and are then eluted from the antibodies in a second step.

Protease inhibitors, such as phenyl methyl sulfonyl fluoride (PMSF), leupeptin, pepstatin or aprotinin may be added at any or all stages in order to reduce or eliminate degradation of proteins in the exosomes during the purification process.

The kit may further include one or more detectable labels as described above for detecting the presence of one or more biomarkers present in the exosomes.

In addition, the kit may contain one or more reagents for preparing an exosome preparation; one or more infectious agent-associated biomarker binding agents selective for one or more infectious diseases or infectious disease conditions; one or more infectious agent-associated biomarker standards, and/or one or more detectable labels for detecting binding of one or more biomarker binding agents to one or more infectious agent-associated biomarkers.

In one embodiment, a sandwich ELISA kit for detecting disease associated biomarkers includes a solid substrate with an anti-ALG6 antibody attached thereto, and at least one disease associated biomarker binding agent, such as a biomarker detection antibody or biomarker specific nucleic acid. The kit may further include a secondary antibody carrying a suitable reporter for quantifying disease associated biomarker levels in the exosome sample, reagents for nucleic acid or protein detection, buffer solutions for dilutions, protein standards, nucleic acid standards, and the like.

The detectable labels for detecting binding of one or more biomarker binding agents to one or more infectious agent-associated biomarkers may include antibody reagents, such as secondary antibody-detectable label conjugates for detection and quantitation of protein levels, as well amplification primers or oligonucleotide probes for detection and quantitation of infectious agent associated genomic nucleic acids, mRNA levels and miRNAs.

In one embodiment, the kit is an HIV detection kit comprising one or more reagents for preparing an exosome preparation; one or more HIV virus biomarker binding agents; one or more HIV virus-associated biomarker standards, and/or one or more detectable labels for detecting binding of one or more HIV virus biomarker binding agents to one or more HIV virus biomarkers. In a related embodiment, the kit includes one or more HIV virus biomarker binding agents bind to one or more HIV proteins selected from the group consisting of Nef, gp120, protease, Vif, Gag-Pol, Gag, p24, Rev, reverse transcriptase (RT), Tat, p1, p17, Vpu, Vpr, gp41 and DNA polymerase.

In another embodiment, the kit is a hepatitis virus detection kit comprising one or more reagents for preparing an exosome preparation; one or more hepatitis virus biomarker binding agents; one or more hepatitis virus biomarker standards, and/or one or more detectable labels for detecting binding of one or more hepatitis virus biomarker binding agents to one or more hepatitis virus biomarkers. In a related embodiment, the hepatitis virus biomarker binding agents bind to one or more hepatitis virus proteins selected from the group consisting of Hep C core antigen, Hep C NS2, Hep C NS3 and Hep C NS4.

The kits described above may additionally include liquids suitable for resuspending exosomes isolated from a bodily fluid sample and one or more container(s) for collecting a bodily fluid sample and/or a centrifuge filter for isolating exosomes from the bodily fluid sample. Additionally, the kits described above will typically include a label or packaging insert including a description of the components or instructions for use. Exemplary instructions include, instructions for collecting a bodily fluid sample, for harvesting exosomes from the sample, and for detecting a disease associated biomarker.

In another aspect, a kit for purifying exosomes includes a solid substrate comprising anti-ALG6 antibodies attached thereto. The kit may further include one or more centrifuge filters (described above) for concentrating exosomes in the bodily fluid samples prior to being applied to the solid substrate. The kit may additionally include liquids suitable for resuspending exosomes isolated from a bodily fluid sample, one or more container(s) for collecting a bodily fluid sample, as well as a label or packaging insert including a description of the components and/or instructions for use. Exemplary instructions include, for example, instructions for collecting and concentrating a bodily fluid sample and immobilizing the exosomes onto the solid substrate.

Methods of Diagnosis

In one aspect, a method for diagnosing a disease or a condition in a subject, comprises the steps of (a) contacting a bodily fluid sample from the subject with an anti-ALG6 antibody under conditions suitable for binding the exosomes to capture agent to form bound exosome-anti-ALG6 complexes; (b) contacting the complexes with at least one disease- or condition-associated biomarker binding agent suitable for detecting at least one disease- or condition-associated biomarkers present in the exosomes; and (c) determining whether the exosomes comprise at least one detectable disease- or condition-associated biomarker, wherein detection of the at least one disease- or condition-associated biomarker in step (c) is indicative of a disease or condition in the subject and wherein lack of detection of the at least one disease- or condition-associated biomarker in step (d) is indicative of the absence of the disease or condition in the subject.

In some embodiments, the disease is a non-infectious disease. In other embodiments, the disease is an infectious disease condition caused by a microorganism. The infectious disease may be acute or chronic. In some embodiments, the disease is a kidney/renal disease. In some embodiments, the disease is a liver disease. In some embodiments, the disease is a heart disease. In some embodiments, the disease is a gastrointestinal disease. In some embodiments, the disease is a cancer. In some embodiments, the disease is a neurodegenerative disease. In some embodiments, the disease is a disease of the respiratory system. In some embodiments, the disease is a disease of the circulatory/humoral system. In some embodiments, the disease is a disease of the nervous system. In some embodiments, the disease is a disease of the endocrine system. In some embodiments, the disease is a disease of the musculoskeletal system. In some embodiments, the disease is a disease of a connective tissue.

The presence of a disease-associated biomarker in the exosomes is indicative of the disease condition in the subject, whereas the absence of a disease-associated biomarker is indicative of the absence of the disease condition in the subject.

In some embodiments, the anti-ALG6 antibody specifically binds a human ALG6 peptide comprising the amino acid sequence of SEQ ID NO: 1.

In some embodiments, the exosomes are first isolated or purified and then contacted with one or more disease-associated biomarker binding agent(s).

In other embodiments, the exosomes are interrogated for the presence of the disease associated biomarkers in exosomes bound to exosome capture agents immobilized on a solid substrate. Exosome capture agents may include antibodies and lectins.

In certain preferred embodiments, anti-ALG6 antibodies are immobilized on a solid substrate, which is directly interrogated for the presence of present in the exosomes bound thereto.

In some embodiments, the presence, absence or expression level corresponding to a disease-associated biomarker in the exosome is detected at the protein level (e.g., by ELISA, Western blot, antibody microarray, etc.).

In other embodiments, the presence, absence or expression level of a disease-associated biomarkers in the exosomes (and/or their expression levels) is detected at the RNA level (e.g., by RT-PCR, QT-PCR, oligonucleotide array, etc.).

Exemplary mammal subjects for use in accordance with the methods described herein include humans, monkeys, gorillas, baboons, and domesticated animals, such as cows, pigs, horses, rabbits, dogs, cats, goats and the like.

1. Isolation of Exosomes

In some embodiments, the exosomes are first isolated or purified and then contacted with one or more disease-associated biomarker binding agents. Exosomes may be isolated by a variety of methodologies, including but not limited to density gradient centrifugation, differential centrifugation, nanomembrane ultrafiltration, immunoabsorbent capture, affinity capture, size-exclusion chromatography, ultracentrifugation, and ultracentrifugation followed by size-exclusion chromatography (UC-SEC), magnetic activated cell sorting (MACS), combination thereof, and the like.

In one embodiment, the isolating step is accomplished by sedimenting exosomes in a bodily fluid sample via centrifugation. The sedimented exosomes are washed and resuspended at a proper concentration for further analysis. In certain embodiments, the sample may be centrifuged at 100,000×g or above for $10^{-120}$ or 60-120 minutes to sediment the exosomes.

In certain embodiments, the exosomes in the bodily fluid sample are precipitated by a two-step centrifugation process that includes a low g force centrifugation to remove calls and other large particles in the body fluid sample and a high g force centrifugation to precipitate the exosomes. In one embodiment, the sample is first centrifuged at 5,000-25,000×g for 5-30 minutes. The supernatant is then transferred to another tube and is centrifuged again at 100,000×g or above for 30-120 minutes to sediment the exosomes. In a preferred embodiment, the bodily fluid sample is first centrifuged at 20,000-22,000×g for $10^{-20}$ minutes. The supernatant is then transferred to another tube and is centrifuged again at 100,000×g for 30-90 minutes to sediment the exosomes. The sedimented exosomes are then resuspended in a liquid medium for further analysis.

The liquid medium can be isotonic, hypotonic, or hypertonic. In certain embodiments, the liquid medium contains a buffer and/or at least one salt or a combination of salts. Buffers can maintain pH within a particular range, for example, between 1 and 12, and are also referred to as pH stabilizing agents. More typically, pH will range within about pH 5.0 to about pH 12.0. A particular example of a pH stabilizing agent is a zwitterion. Specific non-limiting examples of pH stabilizing agents include Tris (hydroxymethyl)aminomethane hydrochloride (TRIS), N-(2-hydroxyethyl) piperazine-N'-2-ethanesulfonic acid (HEPES), 3-(N-morpholino) propanesulfonic acid (MOPS), 2-(N-morpholino) ethanesulfonic acid (MES), N-tris [hydroxymethyl]methyl-2-aminoethanesulfonic acid (TES), N-[carboxymethyl]-2-aminoethanesulfonic acid (ACES), N-[2-acetamido]-2-iminodiacetic acid (ADA), N,N-bis [2-hydroxyethyl]-2-aminoethanesulfonic acid (BES), N-[2-hydroxyethyl]piperazine-N-[2-hydroxypropoanesulfonic acid] (HEPPSO), N-tris [hydroxymethyl]methylglycine (TRICINE), N,N-bis [2-hydroxyethyl]glycine (BICINE), 4-(cyclohexylamino)-1-butanesulfonic acid (CABS), 3-(cyclohexylamino)-1-propanesulfonic acid (CAPS), 3-(cyclohexylamino-2-hydroxy-1-propanesulfonic acid (CAPSO), 2-(cyclohexylamino) ethanesulfonic acid (CHES), N-(2-hydroxyethyl) piperazine-N'-(3-propanesulfonic acid) (EPPS), piperazine-N,N'-bis(2-ethanesulfonic acid (PIPES), [(2-hydroxy-1,1-bis [hydroxymethyl]ethyl)amino]-1-propanesulfonic acid (TAPS), N-tris (hydroxymethyl)methyl-4-aminobutane sulfonic acid (TABS), 2-amino-2-methyl-1-propanol (AMP), 3-[(1,1-dimethyl-2-hydroxyethyl)amino]-2-hydroxypropanesulfonic acid (AMPSO), ethanolamine and 3-amino-1-propanesulfonic acid. Additional specific non-limiting examples of pH stabilizing agents include potassium chloride, citric acid, potassium hydrogenphthalate, boric acid, potassium dihydrogenphosphate, diethanolamine, sodium citrate, sodium dihydrogenphosphate, sodium acetate, sodium carbonate, sodium tetraborate, cacodylic acid, imidazole, 2-Amino-2-methyl-1-propanediol, tricine, Gly-Gly, bicine, and a phosphate buffer (e.g., sodium phosphate or sodium-potassium phosphate, among others).

Buffers or pH stabilizing agents are typically used in a range of about 0.1 mM to about 500 mM, in a range of about 0.5 mM to about 100 mM, in a range of about 0.5 mM to about 50 mM, in a range of about 1 mM to about 25 mM, or in a range of about 1 mM to about 10 mM. More particularly, buffers can have a concentration of about (i.e., within 10% of) 1 mM, 2 mM, 5 mM, 10 mM, 15 mM, 20 mM, 25 mM, 30 mM, 40 mM, or 50 mM.

The liquid medium may further contain a chelating agent. Chelating agents typically form multiple bonds with metal ions, and are multidentate ligands that can sequester metals. Metal sequestration can in turn reduce or prevent microbial growth or degradation of biomolecules (e.g., peptide or nucleic acid), which in turn can improve preservation of biomolecules absorbed to a substrate. Specific non-limiting examples of chelating agents include EDTA (ethylenediamine-tetraacetic acid), EGTA (ethyleneglycol-O,O'-bis(2-aminoethyl)-N,N,N',N'-tetraacetic acid), GEDTA (glycoletherdiaminetetraacetic acid), HEDTA (N-(2-hydroxyethyl)ethylenediamine-N,N',N'-triacetic acid), NTA (nitrilotriacetic acid), salicylic acid, triethanolamine and porphine. Typical concentrations of chelating agents are in a range of about 0.1 mM to about 100 mM, in a range of about 0.5 mM to about 50 mM, or in a range of about 1 mM to about 10 mM.

In some embodiments, the liquid medium may also contain a denaturing agent. Denaturing agents and detergents typically form a chemical bridge between hydrophobic and hydrophilic environments, which in turn disrupt or diminish the hydrophobic forces required to maintain native protein structure. Particular non-limiting chemical classes of denaturing agents and detergents include anionic surfactants, nonionic surfactants, cationic surfactants and ampholytic surfactants. Specific non-limiting examples of detergents include guanidinium thiocyanate, sodium dodecyl sulfate, sodium lauryl sulfate, NP40, Triton X-100, TWEEN™, sodium cholate, sodium deoxycholate, benzethonium chloride, CTAB (cetyltrimethylammonium bromide), hexadecyltrimethylammonium bromide, and N,N-dimethyldecylamine-N-oxide.

The liquid medium may further contain reducing agents and antioxidants to inhibit microbial growth and reduce biomolecule oxidation. Particular non-limiting classes of such agents include free radical scavenging agents. Specific non-limiting examples of reducing agents and anti-oxidants include DTT (dithiothreitol), dithioerythritol, urea, uric acid, 2-mercaptoethanol, cysteine, vitamin E, vitamin C, dithionite, thioglycolic acid and pyrosulfite.

The liquid medium may further contain a preservative or stabilizing agent. Preservatives or stabilizing agents can be used if it is desired to inhibit or delay degradation of an the biomarkers of interest. Specific non-limiting examples of preservatives and stabilizing agents include sodium azide and polyethylene glycol (PEG). Typical concentrations of preservatives and stabilizing agents range from about 0.05% to about 1%.

The liquid medium may further contain one or more protease inhibitors. Protease inhibitors inhibit peptide degradation. Particular non-limiting classes of protease inhibitors include reversible or irreversible inhibitors of substrate (e.g., peptide) binding to the protease. Particular non-limiting classes of protease inhibitors include serine and cysteine protease inhibitors. Specific non-limiting examples of protease inhibitors include PMSF, PMSF Plus, APMSF, antithrombin III, amastatin, antipain, aprotinin, bestatin, benzamidine, chymostatin, calpain inhibitor I and II, E-64,3,4-dichloroisocoumarin, DFP, elastatinal, leupeptin, pepstatin, 1,10-phenanthroline, phosphoramidon, TIMP-2, TLCK, TPCK, trypsin inhibitor (soybean or chicken egg white), hirustasin, alpha-2-macroglobulin, 4-(2-aminoethyl)-benzenesulfonyl fluoride hydrochloride (AEBSF) and Kunitz-type protease inhibitors.

In another embodiment, exosomes in a bodily fluid sample are collected by passing the bodily fluid sample through a filter having a pore size that is smaller than the average size of exosomes. In one embodiment, the filter has a pore size that is smaller than 90 nm. The exosomes are then removed from the filter and resuspended at a proper concentration for further analysis. In certain embodiments, exosomes in the bodily fluid samples are collected using centrifuge filters with a molecular weight cutoff of 500 kd-50 kd. In one embodiment, exosomes in the bodily fluid samples are collected using centrifuge filters with a molecular weight cutoff of 100 kd.

In other embodiments, bodily fluids or cell-free supernatants thereof may be incubated with beads coated with one or more antibodies recognizing marker proteins on the surface of exosome particles. Exemplary exosome surface markers include, but are not limited to MHC class II markers, including those of the HLA DP, DQ and DR haplotypes; CD9, CD63, CD81 and CD82.

For example, exosome surface marker-directed antibodies be attached to magnetic beads, such as those manufactured by Dynabeads® (Dynal, Oslo, Norway) for affinity purification of exosomes. More specifically, exosomes having CD63 on their surface may be isolated using antibody coated magnetic bead particles. Dynabeads® are super-paramagnetic polystyrene beads which may be conjugated with anti-human CD63 antibody, either directly to the bead surface or via a secondary linker (e.g., anti-mouse IgG). The beads may be between 1 and 4.5 µm in diameter.

Antibody coated Dynabeads® may be added to an exosome sample prepared using a volume-excluding polymer and incubated at 2-8° C. or at room temperature from 5 minutes to overnight. Dynabeads® with bound exosomes may then be collected using a magnet. The isolated bead-bound exosomes may then be resuspended in an appropriate buffer, such as phosphate buffered saline, and used for downstream analysis (qRT-PCR, sequencing, Westerns, flow cytometry, etc.). Similar protocols may be used for any other exosome surface marker for which an antibody or other specific ligand is available. Indirect binding methods such as those using biotin-avidin may also be used.

2. Protein-Based Detection Assays

A variety of detection assays may be employed for detection of protein-based biomarkers, including enzyme-linked immunosorbent assay (ELISA), dipstick tests, lateral flow strips, microfluidic devices, and antibody microarrays, antibody microarrays and combination thereof. Alternatively, or in addition, protein detection assays may include mass spectrometry (MS), including liquid chromatography-tandem mass spectrometry (LC-MS/MS), surface enhanced laser desorption/ionization time of flight mass spectrometry (SELDI-TOF-MS), high-pressure liquid chromatography-mass spectrometry (HPLC-MS) and fast protein liquid chromatography (FPLC); fluorescence-activated cell sorter (FACS) analysis, Western blot, de novo protein sequencing (e.g., via LC-MS/MS), one-dimensional and two-dimensional electrophoretic gel analysis and combinations thereof.

ELISA assays may include direct enzyme-linked immunosorbent assays, indirect enzyme-linked immunosorbent assays, direct sandwich enzyme-linked immunosorbent assays, indirect sandwich enzyme-linked immunosorbent assays, and competitive enzyme-linked immunosorbent assays. ELISA assays are typically carried out using antibody coated assay plates or wells.

A modified sandwich ELISA may be used to capture, detect, characterize and quantify exosomes from small volumes of body fluids. An enzyme substrate for an enzyme conjugate or a direct label may provide a colorimetric, chemiluminescent, fluorescent or electrochemiluminescent readout as the detection signal. The signal generated is proportional to the amount of target antigen present in the sample.

The antibody linked label or reporter determines the detection mode. A spectrophotometric plate reader may be used for colorimetric detection. Other types of reporters may be utilized to increase the sensitivity of the assay. For example, chemiluminescent substrates have been developed which further amplify the signal and can be read on a luminescent plate reader. Alternatively, a fluorescent readout may be generated using a fluorophor tagged antibody, whose binding can be measured using a fluorescent plate reader.

Substrates for the detectable label include chromogenic substrates, chemiluminescent substrates, fluorescent or fluorogenic substrates, and electrochemiluminescence substrates.

Exemplary chromogenic substrates include TMB (3,3',5, 5'-tetramethylbenzidine), DAB (diaminobenzidine), AEC (3-amino-9-ethylcarbasole), BCIP/NBT (5-bromo-4-chloro-3-indolyl-phosphate/nitroblue tetrazolium), BCIP/INT (5-bromo-4-chloro-3-indolyl phosphate/iodonitrotetrazolium, o-NPP (o-nitrophenyl phosphate), NF (New fuchsin), FRT (Fast Red TR Salt), ABTS [(2,2'-azino-bis (3-ethylbenzothiazoline-6-sulfonic acid)] and OPD (o-phenylenediamine).

Exemplary chemiluminescent substrates include SuperSignal® ELISA Pico Chemiluminescent Substrate (Thermo Fisher Scientific Inc.); 1,2 dioxetanes, such as 4-methoxy-4-(3-phosphatephenyl)spiro [1,2-dioxetane-3,2'-adamantane] and 3-(2'-spiroadamantyl)-4-methoxy-4-(3"-phosphoryloxy)-phenyl-1,2-dioxetane AMPPD; acridinium (N-sulfonyl) carboxamides, acridan esters, acridan thioesters, enol phosphates, acridan enol phosphates, luminols, and combination thereof.

Fluorescent or fluorogenic substrates include those capable of changes, either individually or in combination, of total fluorescence, excitation or emission spectra or fluorescence resonance energy transfer (FRET).

A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compounds.

Where the enzymatic activity to be detected is horseradish peroxidase (HRP), exemplary fluorogenic substrates include QuantaBlu™ Fluorogenic Peroxidase Substrate (Thermo Fisher Scientific Inc.). Where the enzymatic activity to be detected is beta-D-glucosidase activity, e.g., derived from *Bacillus subtilis*, a preferred fluorogenic enzyme substrate is 4-methylumbelliferyl-beta-D-glucoside as well as various 4-methylumbelliferyl derivatives, such as 4-methylumbelliferyl-2-acetamido-4,6-O-benzylidene-2-deoxy-β-D-glucopyranoside, 4-methylumbelliferyl acetate and 4-methylumbelliferyl-N-acetyl-O-D-galactosaminide; 7-amido-4-methylcoumarin derivatives, and diacetylfluorescein derivatives.

In contrast to chemiluminescent processes, which entail the creation of the luminescent species by a chemical reaction, in an electrochemiluminescent process, a species luminesces upon the exposure of that species to electrochemical energy in an appropriate surrounding chemical environment. In one embodiment, an electrochemiluminescent (ECL) based detection assay is based on a catalytic process employing β-lactamase-conjugated anti-analytes which enzymatically hydrolyze electrochemiluminescent substituted substrates, making them strongly electrochemiluminescent. In this case, the substrate is labeled with an organic ECL detectant or an organometallic ECL detectant, such as rubrene, 9,10-diphenyl anthracene, ruthenium containing compounds, osmium containing compounds and ruthenium II tris-bypyridine chelate.

As the level of the disease associated biomarker is increased, the amount of detection antibody (and detectable label) bound to the exosomes increases, leading to a higher measured response. Known amounts of biomarker proteins may be used to generate a standard curve to provide a quantitative determination of the biomarker level in the sample.

In some embodiments, dipstick assays may be used to detect exosome biomarkers. Dipstick assays utilize a well-established lateral flow format, wherein capture antibodies are striped or banded onto nitrocellulose membrane and a wicking pad draws the sample up through the dipstick, whereby the exosome biomarkers can interact with a suitable biomarker detection antibody, or combination thereof. Other antibodies specific to exosome biomarkers, or other proteins of interest may be included.

In some embodiments, microfluidic devices, also referred to as "lab-on-a-chip" systems, biomedical micro-electro-mechanical systems (bioMEMs), or multicomponent integrated systems, may be used for detecting exosome biomarkers. Such systems miniaturize and compartmentalize processes that allow for detection of exosome biomarkers.

Array-based assays and bead-based assays can be used with microfluidic device. For example, a binding agent can be coupled to beads and the binding reaction between the beads and a biomarker can be performed in a microfluidic device. Multiplexing, or detecting more than one biomarker at once, can also be performed using a microfluidic device. Different compartments can include different binding agents for different populations of biomarkers, where each population has a different bio-signature.

In another embodiment, microarrays are used to detect exosome biomarkers. Microarrays are typically small, high throughput chips generally made of a solid substrate structure, typically glass slides, nitrocellulose, or microtiter plates. Generally, antibodies to specific biomarkers or lectins are bound to the solid substrate; however, other molecules, such as, but not limited to other proteins, aptamers, DNA, RNA, sugars or lipids can be bound to the solid surface as well. Detection of the captured biomarker can be accomplished as discussed above for ELISA detection.

3. Nucleic Acid Based Detection Assays

In some embodiments, the biomarker binding agents may include one or more nucleic acid probe sequences specific for one or more disease associated biomarkers. Exemplary nucleic acids include both single-stranded and double-stranded polynucleotides or oligonucleotides of DNA or RNA. Exemplary nucleic acids include viral genomic DNAs or RNAs, including reverse transcribed derivatives thereof.

In certain embodiments, upon capture of exosomes to a solid substrate, the exosomes can be lysed to release nucleic acids, including DNA and RNA for hybridization to nucleic acid probes specific for one or more disease associated biomarkers of interest. In certain embodiments, the biomarker binding agents include one or more oligonucleotide probes for reverse transcriptase polymerase chain reaction (RT-PCR) amplification of RNAs in the exosomes, including mRNAs, miRNAs and the like.

In other embodiments, isolated exosomes are applied to a plurality of wells in a microarray, where each well contains a different oligonucleotide probe for direct hybridization. Each oligonucleotide probe corresponds to one or more different disease associated biomarkers of interest.

In other embodiments, isolated exosomes are applied to a plurality of wells in a microarray, where each well contains one or more oligonucleotide pairs for PCR amplification of DNAs or reverse transcribed RNAs (i.e., cDNAs) released from lysed exosomes. Each oligonucleotide pair is designed to amplify one or more different disease associated biomarker regions of interest.

Preferred methodologies for determining mRNA or miRNA expression levels include quantitative reverse transcriptase PCR (QT-PCR), quantitative PCR (qPCR), quantitative real-time RT-PCR, oligonucleotide microarrays, nucleotide sequencing or combinations thereof.

In certain embodiments, a diagnosis may include an oligonucleotide microarray for detecting and quantitating one or more miRNA expression level(s). In one embodiment, the oligonucleotide microarray consists of an arrayed series of a plurality of microscopic spots of oligonucleotides, called features, each containing a small amount (typically in the range of picomoles) of a specific oligonucleotide sequence. The specific oligonucleotide sequence can be a short section of a gene or other oligonucleotide element that is used as a probe to hybridize a cDNA or cRNA sample under high-stringency conditions.

Probe-target hybridization may be detected and quantified by fluorescence-based detection of fluorophore-labeled targets to determine relative abundance of nucleic acid sequences in the target. The oligonucleotide probes may be attached to any of the above described solid substrates by e.g., covalent bonding to a chemical matrix (via epoxy-silane, amino-silane, lysine, polyacrylamide or others). The solid surface can be glass or a silicon chip or microscopic beads.

Biological materials which may be extracted from exosomes for biomarker evaluation include proteins, peptides, RNA and DNA, lipids. For example, the mirVana™ PARIS™ Kit (AM1556, Life Technologies) may be used to recover native protein and RNA from exosomes samples, including small RNAs, such as miRNAs, snRNAs, and snoRNAs.

Total RNA may be extracted using acid-phenol chloroform extraction. In certain embodiments, RNA may purified using a glass-fiber filter under conditions that recover small-RNA containing total RNA, or that separate small RNA species less than 200 nucleotides in length from longer RNA species such as mRNA. Because the RNA is eluted in a small volume, no alcohol precipitation step may be required for isolation of the RNA.

In some embodiments, cellular or microbial nucleic acids contained in isolated exosomes may be isolated by conventional RNA or DNA purification methodologies employing e.g., silica gel based spin columns (Qiagen) and the like.

4. Other Methods of Use

The determining step may be based on identifying the presence, absence and/or altered expression profiles of one or more infectious agent-associated biomarker(s) in the isolated exosomes obtained from a bodily fluid sample.

In certain embodiments, the determining step includes a comparison between a disease associated biomarker level in a bodily fluid sample and a threshold level diagnostic of the disease. In other embodiments, the determining step includes a comparison between a disease associated biomarker profile in a bodily fluid sample and a disease associated biomarker profile stored in a database. A diagnosis may be based on the results of this comparison.

In certain embodiments, a disease associated biomarker profile is compared to a corresponding biomarker profile from a bodily fluid sample obtained from a subject without the disease. In certain embodiments, the disease-associated profile includes a plurality of disease-associated biomarkers (e.g., at least 2, at least 3, at least 4, at least 5, at least 10). In this method, the genetic background and pertinent information from the medical record of the subject may also be used in the determining step to make a diagnosis.

In another aspect, a method to monitor the progression of a disease or infectious condition in the subject is based on the presence, absence and/or altered expression profiles of one or more disease-associated biomarker(s) in the isolated exosomes obtained from a bodily fluid sample.

In a related aspect, a method to monitor the course of a disease or infectious condition in a subject includes the steps of (a) measuring the level of one or more biomarkers in exosomes of a first sample obtained from the subject at a first time point; (b) measuring the level of the one or more biomarkers in exosomes of a second sample obtained from the subject at a second time point; (c) comparing the level of the one or more biomarkers at the first time point to the level of the one or more biomarkers at the second time point; and (d) determining the disease progression between the first and the second time point based on the result of step (c).

In another aspect, a method for monitoring the effectiveness of a therapeutic agent in a subject as a function of disease-associated biomarker levels present in the exosomes obtained from a bodily fluid sample. This method includes the steps of: (a) determining a disease associated biomarker profile in the exosomes of a sample obtained from a subject prior to administration of the therapeutic agent; (b) determining a disease associated biomarker profile in the exosomes of one or more samples obtained from the subject after administration of the therapeutic agent; (c) comparing the disease-associated biomarker profile in the pre-administration sample with the disease-associated biomarker profile in the post-administration sample(s); and (d) determining the effectiveness of the therapeutic agent based on a comparative analysis of the biomarker profiles in step (c).

In certain embodiments, the method may further contain the step of altering the administration of the agent to the subject. In accordance with this method, the disease-associated biomarker profile may be used as an indicator of the effectiveness of an agent, even in the absence of an observable phenotypic response.

In a further aspect, a method for purifying exosomes includes the steps of: (a) contacting a bodily fluid sample from a subject with an anti-ALG6 antibody under conditions suitable for binding exosomes in the bodily fluid sample to the anti-ALG6 antibody to form bound exosome-anti-ALG6 complexes; and (b) selectively recovering exosomes from the bound exosome-anti-ALG6 complexes.

In one embodiment, the anti-ALG6 antibodies can be used as a capture agent for purifying exosomes by immunoaffinity chromatography, wherein anti-ALG6 antibodies are loaded onto a suitable antibody binding matrix (e.g., Protein A-Sepharose) for subsequent loading of bodily fluids to the column so that exosomes bind to the antibodies in a first step and are then eluted from the antibodies in a second step to selectively recovering exosomes from the bound exosome-anti-ALG6 complexes.

These steps are usually carried out in an aqueous medium. The anti-ALG6 antibodies may be coupled to a suitable matrix in a gel form which is packed in a cylindrical column, followed by loading the column with bodily fluids or other exosome sources (such as tissues) to substantially adsorb the exosomes to the anti-ALG6 antibody. The adsorbed exosomes can be readily desorbed by changing the pH around the antibody, for example, in the case of antibodies belonging to the IgG class, exosomes may be eluted therefrom at an acid pH, usually, a pH of 2-3, while in the case of an antibody belonging to the IgM class, the exosomes may be eluted at an alkaline pH, usually, a pH of $10^{-11}$.

Protease inhibitors, such as phenyl methyl sulfonyl fluoride (PMSF), leupeptin, pepstatin or aprotinin may be added at any or all stages in order to reduce or eliminate degradation of proteins in the exosomes during the purification process. The kit may further include one or more detectable labels as described above for detecting the presence of one or more biomarkers present in the exosomes.

The present application is further illustrated by the following examples which should not be construed as limiting. The contents of all references, patents and published patent applications cited throughout this application, as well as the Figures and Tables, are incorporated herein by reference.

Example 1: Materials and Methods

Patients

HIV+ patients, at various stages of disease, were recruited for this study from four clinical sites in the Atlanta metropolitan area. Only those patients on dialysis were excluded from this study. All samples were collected in accordance with protocols approved by the Institutional Review Board and the Human Subjects Research Committee at Morehouse School of Medicine, and informed consent was obtained from all patients and healthy volunteers according to the guidelines instituted by the Institutional Review Board. Patients were divided into five groups: African American patients with HIV (AA HIV+), white patients with HIV (White HIV+), patients with HIVAN (HIVAN), African American patients with no HIV but FSGS, and healthy controls. Pertinent information was also collected from the medical record of the patients.

Sample Collection and Storage

Urine samples were collected from patients during routine clinical visits. Clinical data were obtained from the medical record of the patients. Urine was collected in sterile containers and transported back to the laboratory. Urinalysis was performed on each specimen using a MULTISTIX™ 10 SG Reagent Strip (Bayer Corporation, Elkhart, Ind.) and the albumin to creatine ratio determined by a Siemens CLINITEK™ Microalbumin dipstick (Bayer Corp.). The strips were read on a Siemens CLINITEK™ Status instrument (Bayer Corp.). Samples were centrifuged at 2,000×g for 10 minutes to remove whole cells and sediment. The remaining urine samples were aliquoted into 4 ml volumes and stored at −80° C. until they were analyzed.

Isolation of Exosomes

Two methods were evaluated for the isolation of exosomes, either high speed ultracentrifugation or ultrafiltration using a molecular weight cutoff filter. For the ultracentrifugation method, 4 ml of urine were transferred into a polycarbonate centrifuge tube and centrifuged at 21,000×g for 15 minutes. The supernatant was removed and again centrifuged at 100,000×g for 60 minutes to sediment the exosomes. The excess urine was decanted and the pellet was reconstituted in 100 µl phosphate buffered saline (PBS) and stored at 4° C. For the ultrafiltration method, 4 ml of urine were added to an AMICON™ Ultra centrifugal filter device (ULTRACEL™, 100 k cutoff, Millipore, Inc.) and centrifuged at 4,000×g for 20 min in a swinging bucket rotor. One hundred µl of PBS was used to rinse the filter and dilute the retentate. The protein concentration was determined using the bicinchoninic acid protein assay (Pierce).

Surface Enhanced Laser Desorption Ionization Time of Flight Mass Spectrometry (SELDI-TOF-MS)

Normal phase chips (PROTEINCHIP™ N120; Ciphergen Biosystems, Fremont, Calif.), that bind proteins through hydrophilic and charged residues were used for the analysis. Five µl of vesicle preparation was applied in duplicate to the chip and incubated for 30 minutes in a humid chamber. Chips were washed three times with 5 µl high-performance liquid chromatography (HPLC)-grade water and air dried for 10 minutes. Saturated sinapinic acid (SPA, Ciphergen Biosystems, CA) were prepared in 50% acetonitrile/0.5% trifluoroacetic acid according to manufacturers instructions. 1 µl of matrix solution (SPA) to each spot and air-dried and subsequently read with the PROTEINCHIP™ Reader II, (Ciphergen Biosystems) using the following settings: laser intensity 250; detector sensitivity 10; high mass 300 Kda, optimized from 3 Kda to 50 Kda. The data acquisition method was set to automatic laser adjustment and peaks were auto identified from 3 Kda and 50 Kda.

Liquid Chromatography-Tandem Mass Spectrometry (LC-MS MS)

Collected exosomes were analyzed by LC/MS using an LTQ mass spectrometer (ThermoFinnigan). The pelleted exosomes were first extracted with 2 D gel loading buffer (Q-biosciences) made fresh the day of analysis. The solubilized pellet was then precipitated using four volumes of ice-cold (−20° C.) acetone and incubated overnight at −20° C. The precipitate was collected by centrifugation at 19,200×g. The pellet was dried and re-dissolved into 50 mM ammonium bicarbonate (AmBIC). The protein solution was first reduced using 2 µl of a 500 mM stock of DTT (Q biosciences, single use) at 56° C. for 30 minutes. The solution was then alkylated by adding 2 µl of a 1M stock of iodacetic acid (IAA; Q-biosciences, single use) and incubating at room temperature for 30 minutes in the dark. A fresh vial of trypsin (Promega Gold mass spec grade) was diluted 8 µl to 312 µl in 50 mM AmBic and kept on ice. Ten microliters of the diluted trypsin was then added to the reaction and it was incubated at 37° C. for 4 hours with shaking. Then 50 µl of 0.5% formic acid was added and the mixture was either directly analyzed or stored at −20° C. for analysis. Ten microliters of sample was injected using an automated sampler onto a CAPTRAP™ (Michrom) C18 peptide trap at a flow of 10 µl per min. After 10 min the flow was switched to a 0.5 mm×50 micron C18 column (Michrom). Peptides were eluted using a linear gradient of 5-40% acetonitrile in water over 50 min. The eluted peptides were directly introduced into an LTQ mass spectrometer using microspray ionization (Michrom Advance) at a flow rate of approximately 3 µl per min. Samples were analyzed using Excalibur 2.2 software set to analyze ions in a data dependent scanning mode. A precursor scan was followed by data dependent scans of the three most intense ions. Files were searched against a subset of the NR database that included Human and HIV proteins using BioWorks 3.1 (ThermoFinnigan). The threshold for DTA generation was set at 200 and the tolerance for peptides was set at 0.5 Da and proteins at 1.0 Da. Initial protein identification lists were generated using consensus scores of >10.0 and Xcorr scores >1.0.

Electrophoresis and Western Blot

SDS PAGE electrophoresis. Samples were heated at 85° C. for 2 minutes in a Tris-Glycine SDS sample reducing buffer and loaded in a 4-12% Criterion XT Bis-Tris precast acrylamide gel (BioRad, Hercules, Calif.). Approximately 200 ng of sample were loaded into each well. Controls consisted of recombinant HIV Nef (gift of Dr. Andrea Raymond) and HIV recombinant p24 (Immunodiagnostics, Inc.) that were loaded at 30 to 40 ng per well. The gels were stained using Gel Code Blue (Pierce, Inc.) or the proteins were transferred to PVDF membrane (Immobilon-P, Millipore Corp, Billerica, Mass.) for Western Blot analysis. The SNAP ID system (Millipore, Corp) was used for the western blot analysis for the presence of either HIV Nef or HIV proteins. HIV Nef identification was performed using a monoclonal mouse anti-HIV Nef monoclonal antibody (1:1500, Chemicon Int., CA) and a secondary antibody, goat anti-mouse IgG (H+L) peroxidase conjugated antibody (1:15,000, Jackson Immunoresearch, West Grove, Pa.). HIV proteins were detected using pooled human HIV+ serum (1:15,000) as the primary antibody and a goat anti-human IgG (H+L) peroxidase conjugated antibody (1:15,000, Jackson Immunoresearch). The membrane was incubated with a chemiluminescent substrate (SuperSignal West Femto Maximum, Pierce, Inc.) and exposed to X-ray film (CL-Xposure, Kodak) and developed.

Transmission Electron Microscopy

Samples were fixed in 2.5% glutaraldehyde in 0.1M cacodylate buffer for 2 hours at 4° C. followed by 2 washes with 0.1M cacodylate buffer, 5 minutes each. The samples were fixed again with 1% osmium tetroxide in 0.1M cacodylate buffer for 1 hour at 4° C. followed by 2 washes with the cacodylate buffer and 3 washes with deionized water, 5 minutes each. Thin sections were cut, stained with 0.5% aqueous uranyl acetate for 2 hours at room temperature, and viewed with a JEOL 1200EX transmission electron microscope.

Example 2: Isolation of Urinary Vesicles, Ultracentrifugation Versus Ultrafiltration Vesicles from the urine of six (6) different HIV+ patients were isolated by ultracentrifugation or ultrafiltration to determine which of the two methods yielded the greatest amount of protein. The ultrafiltration method consistently isolated more protein (2930 μg median) than the ultracentrifugation method (591 μg, median).

Example 3: SELDI-TOF-MS Analysis of HIV-Associated Biomarkers in Urinary Exosomes from Patients FIG. 1 is a flow chart showing an embodiment of an exemplary method for detecting HIV-infection or monitoring the progress of HIV-infection in a subject using a urine sample from the subject. Urinary exosomes from patients of various groups were analyzed for the presence of HIV-associated biomarkers by SELDI-TOF-MS. The results are confirmed by LC-MS/MS. Spectrum of SELDI-TOF-MS from representative patients is shown in FIGS. 2-6. Table 1 summarizes HIV-associated proteins that were detected by SELDI-MS and confirmed by LC-MS/MS in different test groups. Table 2 summarizes the urine protein profiles in individual patient.

TABLE 1

HIV-associated proteins detected in urine samples by SELDI-MS

| Patient | MW | Protein |
|---|---|---|
| HIVAN | 10,585 | HIV envelope gp; HIV Protease |
|  | 23,546 | HIV envelope gp; HIV Nef, HIV Vif |
|  | 33,464 | HIV protein gp; mu A03009B12Rik Protein |
|  | 45,632 | HIV envelope gp; HIV pol protein |
|  | 66,587 | HIV envelope gp; HIV Nef; PgD synthase |
|  | 78,942 | Unknown |
| AA HIV | 23,684 | HIV envelope gp; HIV Nef; PgD synthase |
|  | 83,256 | Unknown |
| FSGS | 66,533 | Unknown |
| White HIV | 23,935 | Unknown |

TABLE 2

Urine protein profiles in individual patient

| ID | Diagnosis | Race | CD4 | VL | Nef | Gag | Pol | Protease | Rev | RT | Tat | Vif | pl | p24 | P17 | poly |
|---|---|---|---|---|---|---|---|---|---|---|---|---|---|---|---|---|
| 22 | HIVAN | AA |  |  | X | X | X | X | X |  | X | X | X | X | X |  |
| 27 | HIV/AIDS | AA | 134 | <50 | X |  |  |  |  |  |  |  |  |  |  |  |
| 28 | HIV/AIDS | AA | 134 | 19,800 | X |  |  | X |  | X |  | X |  |  |  |  |
| 30 | HIV/AIDS | AA | <20 | <10,000 | X | X | X | X |  | X | X | X |  | X | X | X |
| 41 | HIV | AA | 440 | 29,187 | X | X | X |  |  |  |  |  |  |  |  |  |
| 46 | HIV | AA | 689 | <50 | X | X | X |  | X | X |  |  |  |  |  |  |
| 62 | HIV | AA | 232 | <50 | X |  |  |  |  |  |  |  |  |  |  |  |
| 63 | HIV/AIDS | AA | 83 | 2,023 | X |  |  |  |  |  |  |  |  |  |  |  |
| 70 | HIV | AA | 990 | <50 | X |  |  |  |  |  |  |  |  |  |  |  |
| 104 | HIV | AA | 313 | 77 | X | X |  |  |  |  |  |  |  |  |  |  |
| 111 | HIV/AIDS | AA | 182 | <50 |  | X | X |  |  |  |  |  |  |  |  |  |
| 112 | HIV | AA | 584 | <200 |  |  | X |  |  |  |  | X |  |  |  |  |
| 48 | HIV | W | 454 | 52000 | X |  |  |  | X |  | X | X |  |  |  |  |
| 86 | HIV | W | 1642 | <75 | X | X | X | X |  |  |  |  |  |  |  |  |
| 103 | HIV | W | 560 | 150 | X | X | X |  |  |  |  |  |  |  |  |  |
| 106 | HIV | W | 302 | <50 |  |  |  |  |  |  |  |  |  |  |  |  |
| 108 | HIV | W | 653 | <50 | X | X | X |  |  |  |  |  |  |  |  |  |
| 110 | HIV | W | 379 | <50 | X | X |  |  |  |  |  |  |  |  |  |  |

TEM was used to visualize the patients' vesicles from urine. Exosomes were isolated from 4 ml of urine, fixed and embedded for TEM. The figure shows distribution of vesicles in: A) HIVAN; B) focal segmental glomerulosclerosis; C) AA HIV+; and D) white HIV+; E) AA HIV negative. HIVAN, FSGS and AA HIV+ patients clearly have a higher population of vesicles compared to white HIV+ patients and AA normal patients.

Ingenuity Pathways Analysis

As shown in Examples 1 and 2, the SELDI-TOF-MS peaks of AA HIV+ patients exhibited exceedingly similar protein patterns to those of HIVAN patients and slightly similar patterns to FSGS patients, suggesting that the AA HIV+ patients whose peaks were similar to those of HIVAN may be predisposed to developing HIVAN. The baseline protein value (30-2000 mg/dl) for the FSGS patients and AA HIV+ patients was in the same range. Similar to the protein values for HIVAN, but unlike FSGS patients, the proteins detected in AA HIV+ patients were analogous to those of HIVAN patients. This underscores the significance that HIV infection, with or without the presence of renal disease, is still largely responsible for development of HIVAN; and a prior condition of renal insufficiency before HIV infection is not a necessary prerequisite for the development of HIVAN.

Unlike AA HIV+ patients, protein profiles of white HIV+ patients were a stark contrast to the protein profiles of HIVAN patients. It suggests that factors other than simple infection of renal cells or the infiltration of infected immune cells in renal tissue probably mediate the expression of nephropathy. The number of AA HIV+ and HIVAN (12/15) patients that had detectable Nef using LC-MS/MS piggybacks on the earlier assertion about the similarities between the kidney pathologies of transgenic mice expressing Nef and HIVAN patients, hinting that Nef may be involved in causing kidney damage to HIV patients. This may explicate the relationship, if any, between the similarity in the kidney pathology of transgenic mice expressing Nef and HIVAN patients, and the similarity between the expression of Nef in the protein profiles of AA HIV+ and HIVAN patients. It may also shed additional insight as to what role Nef plays in the pathogenesis of HIVAN. HIV envelope gp was also detected by LC-MS/MS in HIVAN and AA HIV+ patients. Although local HIV infection of the kidney may have implications beyond development of HIVAN, with kidney serving as a potential viral reservoir, a corollary would be that some of these viruses in the reservoir would find their way in the urine.

The transmission electron microscopy (FIG. 7) shown in the urine of AA HIV+, FSGS and HIVAN patients' conspicuous vesicles were not evident in the urine of white HIV+ and AA normal patients. The HIVAN exosome solution was diluted 10 fold because the initial visualization expressed an exceedingly dense population of exosomes that was difficult to visualize, suggesting that HIVAN patients may be producing vesicles at an increasing rate than all the other patient groups. The HIV-associated kidney damage may responsible for this marked increase in exosome excretion in AA HIV+ and HIVAN patients.

Figure 8:
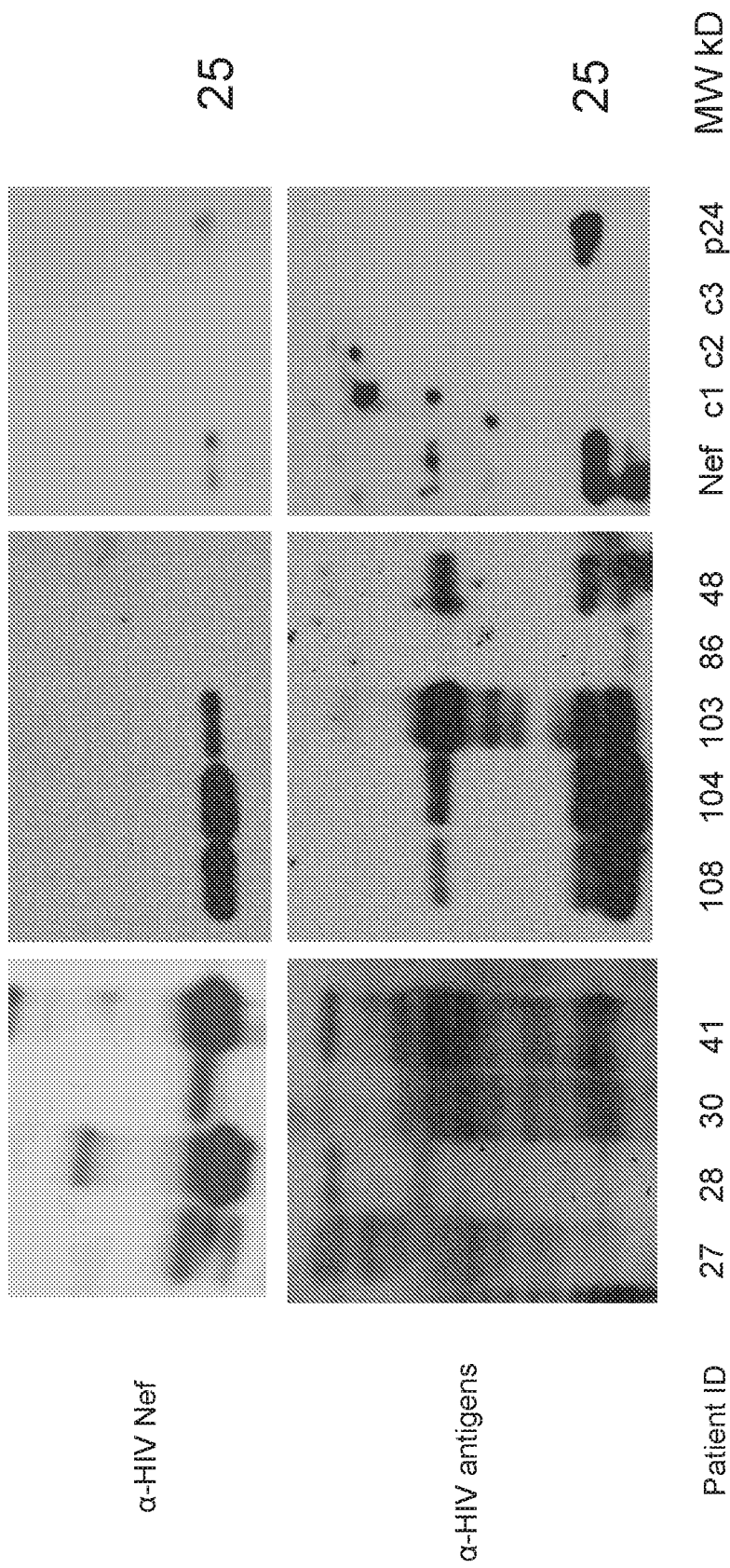
FIG. 8 is a composite of pictures showing Western blot analysis of urinary vesicles from HIV+ patients and controls. Vesicles were isolated from urine by ultrafiltration and analyzed for the presence of HIV Nef or other HIV proteins. The top panel used anti-HIV Nef monoclonal antibodies, while the lower panel utilized pooled HIV+ patient sera s the primary antibodies. Patients 27, 28, 30, 41 and 104 were AA. Patients 108, 103, 86 and 48 were HIV+ white patients. The last panel is control panel for three HIV negative individuals, recombinant HIV Nef and p24.

Example 4: Western Blot Analysis, Validation of the Presence of HIV NEF and Other HIV Proteins Urinary vesicle samples from fourteen (14) HIV+ AA and nine (9) HIV+ white patients were isolated using ultrafiltration and analyzed for the presence of HIV Nef and other HIV proteins using western blot analysis. All the HIV+ AA samples were positive for HIV Nef by western blot, although HIV Nef was not detected in sample 41 by mass spectrometry (FIG. 8). This discrepancy could be caused by the isolation method utilized for the mass spectrometry analysis, which was ultracentrifugation, and yields less protein. HIV Nef was only identified in four (4) HIV+ white patients while mass spectrometry identified three (3) samples without HIV Nef. All HIV+ patients had detectable HIV proteins by western blots, but had varying kinds and amounts (FIG. 8).

Example 5: Sandwich ELISA Analysis of HBV Biomarkers in Urinary Exosomes from Patients Exosome ELISA The Nunc 96 strip well ELISA plates coated with 100 µl of µg/ml GNA and blocked with Blocking Buffer were washed 1× with 250 µl of Wash Buffer (0.1% TWEEN™-20 in PBS). Positive controls (mannan from *S. cerevisiae*) and samples were added to the plates in the amount of 100 µl/well and incubated for 1 hour at room temperature. The plates were washed 1× with 250 µl of Wash Buffer. 100 µl of HRP labeled GNA (1 ug/ml) or an antibody specific to a marker on the exosome of interest were added to each well and incubated for 1 hour at room temperature. The plates were washed 4× with 250 µl of Wash Buffer. 100 µl of Tetramethylbenzidine (TMB) were added to each well and incubated for 30 minutes at room temperature or until the Blank well begins to show color. The reaction was stopped by adding 100 µl of 1M $H_2SO_4$ to each well. The plates were read in an ELISA plate reader at 450 nm. Serial dilution of samples or antibodies was made with Diluent Buffer (1% BSA, 0.1% TWEEN™-20 in PBS). Marker specific-antibodies include the following:

Anti-Hepatitis C NS4b antigen antibody, mouse monoclonal (MA1-7358, Thermo Scientific);
Anti-Hepatitis C NS3 antigen antibody, mouse monoclonal (MA1-7357, Thermo Scientific);
Anti-Hepatitis C Core antigen antibody, mouse monoclonal (ab2582, Abcam);
Anti-Hepatitis C Core antigen antibody, mouse monoclonal (MA1-080, Thermo Scientific);
Anti-Hepatitis C NS3 antigen antibody, mouse monoclonal (MA1-21376, Thermo Scientific);
Anti-Hepatitis C NS4 antigen antibody, mouse monoclonal (MA1-91550, Thermo Scientific);
Anti-Hepatitis C NS5a antigen antibody, mouse monoclonal (MA1-7368, Thermo Scientific);
Anti-Hepatitis A virus antibody, goat polyclonal (LS-C103171, Lifespan Biosciences);
Anti-Hepatitis B virus antibody, goat polyclonal (LS-C5624, Lifespan Biosciences);
Anti-ALG6 antibody, a rabbit polyclonal directed against a synthetic peptide corresponding to a region within the peptide YEAQRHWQEIT (SEQ ID NO: 1) from Human ALG6 (alpha-1,3-glucosyltransferase).

Example 6: Sandwich ELISA Analysis of HBV Biomarkers in Urinary Exosomes from Patients Urinary exosomes isolated from hepatitis patients and normal controls were analyzed for the presence of hepatitis A virus (HAV), hepatitis B virus (HBV) and hepatitis C virus (HCV)-associated biomarkers by exosome ELISA.

Figure 9:
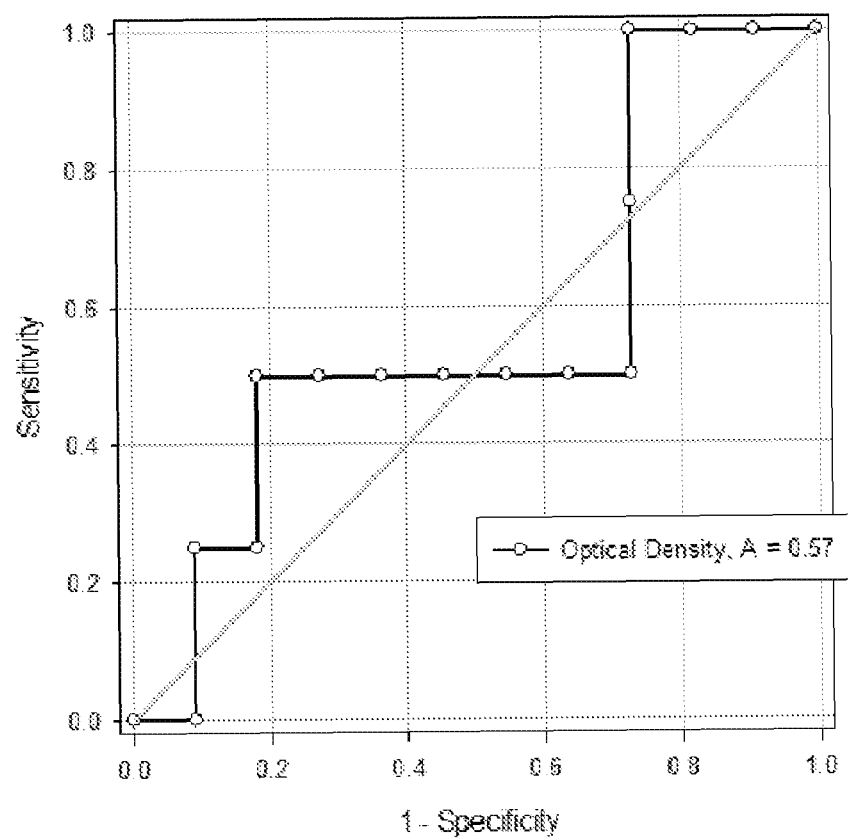
FIG. 9 is a receiver operating characteristic (ROC) curve for hepatitis B diagnosis based on exosome ELISA.

FIG. 9 shows the receiver operating characteristic (ROC) curve for diagnosis of hepatitis B using anti-Hepatitis B antibody in the exosome ELISA.

Figure 10:
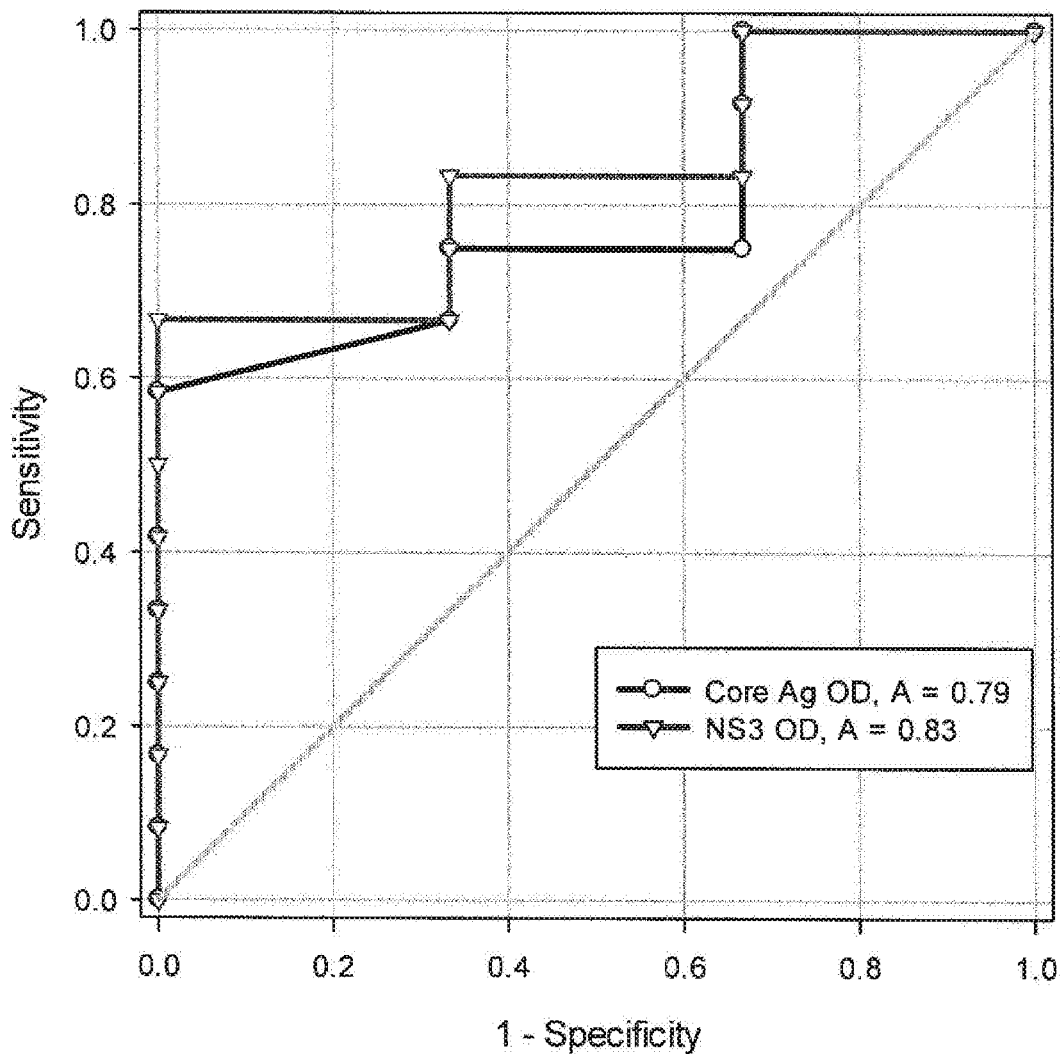
FIG. 10 is a ROC curve for hepatitis C diagnosis based on exosome ELISA.

FIG. 10 is a ROC curve for diagnosis of hepatitis C using HCV core antigen and HCV NS3 protein as the biomarkers for hepatitis C in the exosome ELISA.

Example 7: Sandwich ELISA Analysis of HIV-1 Biomarkers in Urinary Exosomes from Patients Urine Collection: A total of 147 urine samples were collected for this study. The samples were obtained from Morehouse Medical Associates, AIDS Atlanta, Absolute Care, Morehouse School of Medicine and Grady Memorial Hospital, all in the Atlanta metropolitan area, as well as Faith Alive Foundation in Jos, Nigeria. Sample were obtained from 86 HIV positive samples, 21 AIDS samples, 4 HIVAN samples, 5 CKD samples, and 31 healthy samples. IRB approval was obtained from the institutional review board, Morehouse School of Medicine, Atlanta, GA 30310, on the use of human samples for research. All patients signed informed consent forms.

At the time of sample collection all of the AIDS patients were on HAART, 50% of the HIVAN patients were on HAART, while 42% of the patients with only HIV infection were on HAART. Also, all 147 participants were screened for HIV infection prior to the start of the study, using the GS HIV-1 Western Blot validation kit (Bio-Rad Laboratories, Hercules, CA), and the participants with HIV burden (HIV-only, AIDS and HIVAN) were confirmed to have HIV antibodies, while the participants without HIV burden (CKD and healthy) were confirmed negative. All samples collected from participants were analyzed within a 24 hour timeframe.

The urine samples were collected in sterile-urine collection cups and centrifuged at 1000×g to remove cells and sediment. Urinalysis was performed on each sample using MULTISTIX™ Reagent Strip (Siemens Medical, Malvern, PA) and the albumin to creatinine ratio was determined using Siemens CLINITEK™ Microalbumin dipstick (Siemens Medical, Malvern, PA). The samples were stored at −80° C., after initial analysis.

Urinary exosome visualization by transmission electron microscopy: To confirm the existence of these exosomes in urine, they were isolated by filtration with AMICON™ Ultra-4 100 kDa centrifugal filter unit (Millipore, Billerica, MA). In order to visualize them at a high resolution, they were fixed, stained and subsequently viewed with a JEOL 1200EX transmission electron microscope (JEOL, Peabody, MA).

Exosome Isolation for Mass Spectrometry Analysis: The urinary exosomes were isolated by centrifugal filtration of 4 ml of urine, using AMICON™ Ultra-4 100 kDa centrifugal filter unit (Millipore, Billerica, MA), at a speed of 3000 rcf (3000×g) for 15 minutes at 4° C. The retentate (containing exosomes) was collected from the top of the filter, and resuspended in 200 µl phosphate buffered saline.

Mass Spectrometry Analysis: 50 µl of the collected protein containing urinary exosomes were trypsinized, and the sequence of peptides determined by Tandem mass spectrometry (LC/MS/MS), using the LTQ Mass Spectrometer (Thermo Fischer Scientific, Waltham, MA). The resulting peptides were analyzed by the viral database, and initial protein identification lists generated, using consensus scores greater than 10.0, and Xcorr scores greater than 1.0. Also, false discovery rates were determined and set based on the control samples.

Enzyme Linked Lectin Specific Assay: A 96-well plate, coated with snow drop lectin (Aethlon Medical, San Diego, CA) was used and 50 µl of urine was added to the wells in triplicate. After a one hour incubation, goat-anti human HIV polyclonal antibody (1:500, Lifespan Biosciences, Seattle, WA), HIV-1 Nef (NIH AIDS Reagent Program, Germantown, MD) and Vif monoclonal antibodies (Santa Cruz, Dallas, TX) and HIV-1 Vpu (NIH AIDS Reagent Program, Germantown, MD) and Vpr polyclonal antibodies (NIH AIDS Reagent Program, Germantown, MD) were used as primary antibodies, while rabbit-anti goat HRP antibody (1:5000, Bio-Rad, Hercules, CA) and goat-anti mouse HRP antibody (1:5000, Bio-Rad, Hercules, CA) were used as secondary antibodies. Tetramethyl benzidine (Bio-Rad, Hercules, CA) was the substrate for detection, and sulphuric acid (1M, Fischer Scientific, Waltham, MA) was used to stop the reaction. The plate was read at 450 nm, using a spectrophotometer (SPECTRAMAX™ 250, Molecular Devices, Sunnyvale, CA) to determine the optical densities (O.D.) of each sample. This assay distinguished between the optical densities of HIV infected and HIV negative urine with a sensitivity of 100% CI 96.70-100, and a specificity of 97.22% CI 85.42-99.54 in a total sample size of 147 using receiver operating characteristic (ROC) curve, with an area of 0.98.

Enzyme linked anti-ALG6 antibody assay: An anti-ALG6 antibody was produced by Rockland Immunochemicals, Limmerick, PA. Two rabbits were injected with conjugated Ac-YEAQRHWQEIT (SEQ ID NO: 1)-Ahx-C peptide derived from the amino sequence of human ALG6. The anti-serum was not purified in any way.

Enzyme linked anti-ALG6 antibody assay protocol:
1. Open plate, remove number of strips needed to perform test.
2. Wash wells 1× with 200 µl of wash buffer (ELISA wash buffer, Immunochemistry Technologies, Bloomington, MN).
3. Add 50 µl urine and 50 µl diluent buffer (ELISA diluent buffer, Immunochemistry Technologies, Bloomington, MN) to appropriate wells (1:2 dilution), then incubate for 1 hour at room temperature
4. Add 100 µl of anti-HIV detection antibody to each well and incubate for 1 hour at room temperature. The detection antibody is a goat anti-HIV antiserum recognizing disrupted, purified virions and whole virus. The antiserum reacts with all major viral proteins including p17, p24, p53, p64, gp120 and gp160, and does not cross react with T4+ human lymphocytes. This detection antiserum was diluted at 1:500. Monoclonal abs, such as HIV-1 Vif (Santa Cruz), were diluted at 1:1000.
5. Wash plate 2× with 200 µl of wash buffer
6. Add 100 µl of secondary antibody (1:5000 dilution with rabbit anti-goat or goat anti-mouse) to each well and incubate for 1 hour at room temperature
7. Wash plate 2× with 200 µl wash buffer.
8. Add 100 µl Tetramethylbenzidine (TMB) and incubate at room temperature for 15 mins or until blank begins to show color.
9. Stop the reaction with 100 µl of 1M $H_2SO_4$ and read in plate reader at 450 nm.

This assay was more reproducible and required less incubation time than the Enzyme Linked Lectin Specific Assay.

Western Blot Analysis

As a confirmatory test for the presence of HIV-1 proteins in urinary exosomes, a Western blot analysis was carried out. The results indicate the presence of HIV-1 proteins, using HIV-1 polyclonal antibodies and HIV-1 Nef monoclonal antibodies.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following embodiments. The embodiments are intended to cover the components and steps in any sequence which is effective to meet the objectives there intended, unless the context specifically indicates the contrary.

What is claimed is:

1. A method for diagnosing a disease or a condition in a subject, comprising:
    (a) contacting a bodily fluid sample from the subject with rabbit anti-human ALG6 polyclonal antibodies under conditions suitable for forming complexes comprising exosomes bound to the polyclonal antibodies,
    (b) contacting the complexes with at least one disease- or condition-associated biomarker binding agent suitable for detecting at least one disease- or condition-associated biomarkers present in the exosomes; and
    (c) determining whether the exosomes comprise at least one detectable disease- or condition-associated biomarker,
    wherein detection of the at least one disease- or condition-associated biomarker in step (c) is indicative of a disease or condition in the subject and wherein lack of detection of the at least one disease- or condition-associated biomarker in step (c) is indicative of the absence of the disease or condition in the subject,
    wherein the rabbit anti-human ALG6 polyclonal antibodies are made by administering an Ac-YEAQRHWQEIT (SEQ ID NO:1)-Ahx-C synthetic peptide conjugate to a rabbit and purifying the resultant antibodies.

2. The method of claim 1, wherein the polyclonal antibodies in step (a) are attached to a solid substrate.

3. The method of claim 1, wherein prior to step (a) the bodily fluid sample is passed through a centrifuge filter suitable for isolating and concentrating exosomes, wherein the filter has a pore size smaller than 90 nm.

4. The method of claim 1, wherein the at least biomarker binding agent comprises at least one detection antibody specific for a disease- or condition-associated biomarker.

5. The method of claim 4, wherein the step of detection of the at least one disease- or condition-associated biomarker further comprises the step of contacting the detection antibody with a secondary antibody binding to the detection antibody, wherein the secondary antibody comprises a detectable label.

6. The method of claim 1, wherein the at least one biomarker binding agent comprises at least one nucleic acid specific for a disease- or condition-associated biomarker.

7. The method of claim 1, wherein the bodily fluid sample comprises blood or plasma.

8. The method of claim 1, wherein the bodily fluid sample comprises urine.

9. The method of claim 1, wherein the disease or condition is a viral infection.

10. The method of claim 9, wherein the viral infection is hepatitis C virus (HCV) infection.

11. The method of claim 10, wherein the at least one detectable disease- or condition-associated biomarker comprises an HCV protein.

12. The method of claim 11, wherein the HCV protein is selected from the group consisting of HCV NS3 protein, HCV NS4a protein, HCV NS4b protein, HCV NS5a protein, and HCV NS5b protein.

* * * * *